(12) United States Patent
Stokes et al.

(10) Patent No.: US 10,675,108 B2
(45) Date of Patent: Jun. 9, 2020

(54) SURGICAL CLIP APPLIER WITH CLIP FORMING SYSTEM

(71) Applicant: Ethicon LLC, Guaynabo, PR (US)

(72) Inventors: Michael J. Stokes, Cincinnati, OH (US); Matthew Kuhn, Cincinnati, OH (US); Jeffery Bruns, Cincinnati, OH (US); Joshua Young, Loveland, OH (US); Alex Cuti, Cincinnati, OH (US); John Brady, Cincinnati, OH (US); Gregory Scott, Cincinnati, OH (US); Disha Labhasetwar, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 141 days.

(21) Appl. No.: 15/889,610

(22) Filed: Feb. 6, 2018

(65) Prior Publication Data
US 2019/0239970 A1 Aug. 8, 2019

(51) Int. Cl.
*A61B 17/128* (2006.01)
*A61B 34/37* (2016.01)
(Continued)

(52) U.S. Cl.
CPC ............ *A61B 34/37* (2016.02); *A61B 17/122* (2013.01); *A61B 17/1285* (2013.01); *A61B 34/35* (2016.02); *A61B 2017/00199* (2013.01); *A61B 2017/00398* (2013.01); *A61B 2017/00477* (2013.01); *A61B 2017/00526* (2013.01); *A61B 2017/00946* (2013.01); *A61B 2017/2927* (2013.01); *A61B 2017/2929* (2013.01); *A61B 2017/2936* (2013.01); *A61B 2034/305* (2016.02); *A61B 2090/034* (2016.02)

(58) Field of Classification Search
CPC . A61B 17/1285; A61B 17/128; A61B 17/122; A61B 17/1222; A61B 17/068; A61B 17/0682; A61B 17/04; A61B 2017/0411; A61B 2017/042; A61B 2017/0454
See application file for complete search history.

(56) References Cited

U.S. PATENT DOCUMENTS 4,648,542 A * 3/1987 Fox .................... A61B 17/0682
227/19
8,403,945 B2 3/2013 Whitfield et al.
(Continued)

FOREIGN PATENT DOCUMENTS

GB 1345394 A 1/1974

OTHER PUBLICATIONS

ISR/WO from PCT/IB2019/050346 (that claims priority to the present application) dated Apr. 17, 2019.

*Primary Examiner* — Katherine M Rodjom
(74) *Attorney, Agent, or Firm* — Vorys, Sater, Seymour and Pease LLP

(57) ABSTRACT

An end effector for a surgical clip applier includes an elongate body, a clip forming system positioned within the body and arranged to receive an unformed surgical clip, and an actuation mechanism operatively coupled to the clip forming system to actuate the clip forming system and thereby bend the unformed surgical clip into a tissue-ready surgical clip. First and second jaw members are positioned at a distal end of the body and arranged to receive the tissue-ready surgical clip for crimping.

20 Claims, 23 Drawing Sheets

(51) Int. Cl.
  *A61B 17/122* (2006.01)
  *A61B 17/00* (2006.01)
  *A61B 17/29* (2006.01)
  *A61B 34/35* (2016.01)
  *A61B 34/30* (2016.01)
  *A61B 90/00* (2016.01)

(56) References Cited

U.S. PATENT DOCUMENTS

| | | |
|---|---|---|
| 9,232,979 B2 | 1/2016 | Parihar et al. |
| 2009/0125038 A1* | 5/2009 | Ewers .................. A61B 17/122 606/142 |
| 2011/0224696 A1 | 9/2011 | Huitema et al. |
| 2014/0005695 A1 | 1/2014 | Shelton, IV |
| 2015/0073439 A1 | 3/2015 | Dannaher |
| 2016/0287252 A1 | 10/2016 | Parihar |

* cited by examiner

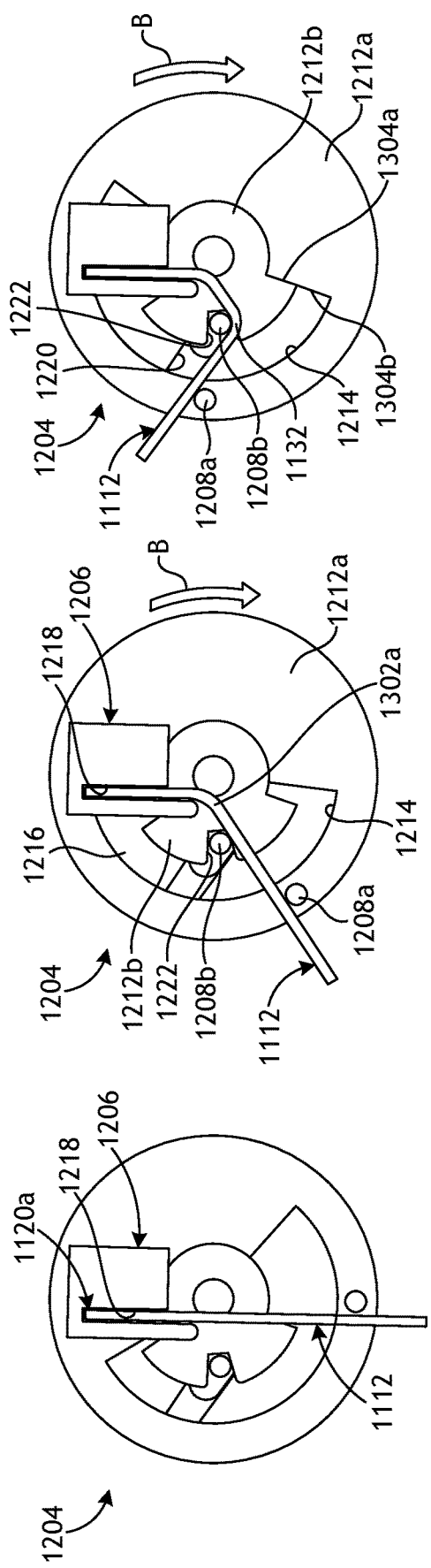
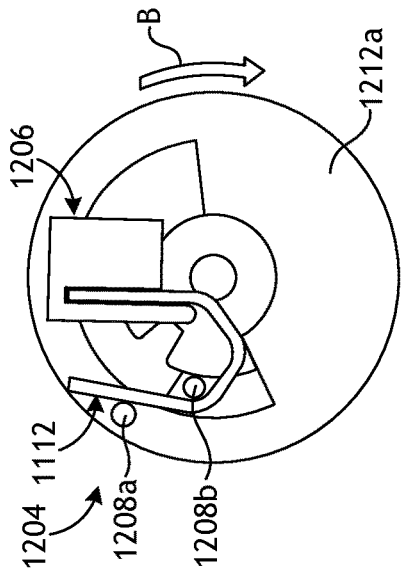
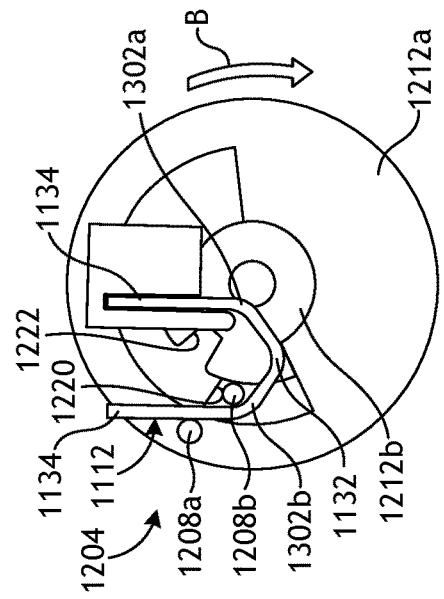
FIG. 13A  FIG. 13B  FIG. 13C  FIG. 13D  FIG. 13E

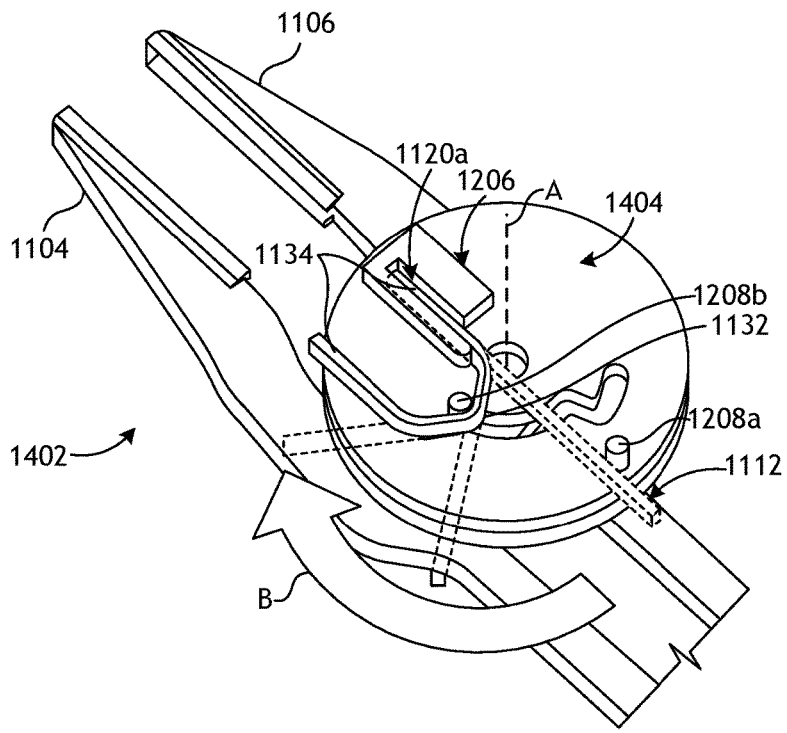
*FIG. 14A*
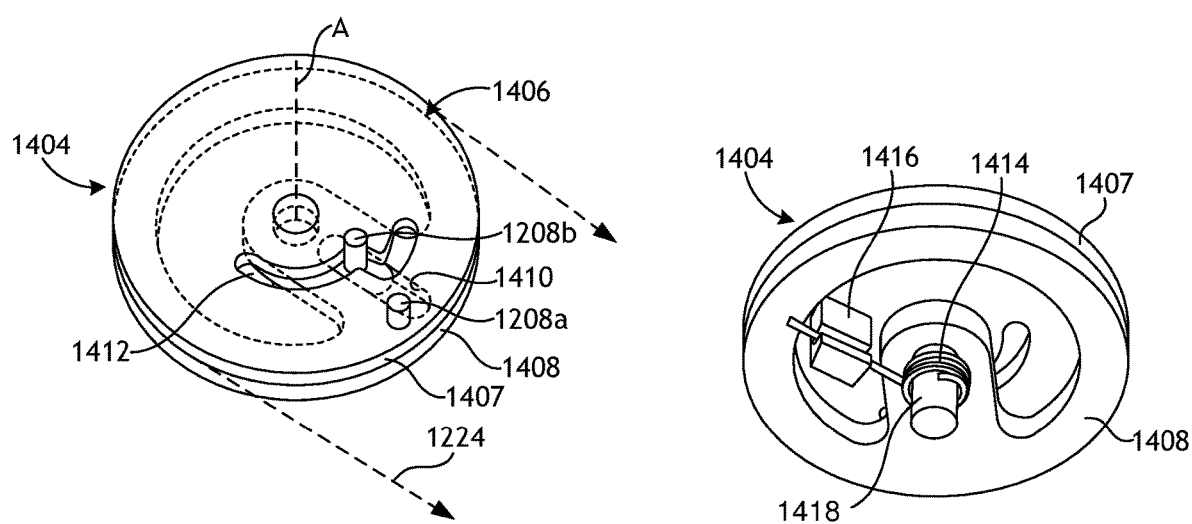
*FIG. 14B*   *FIG. 14C*

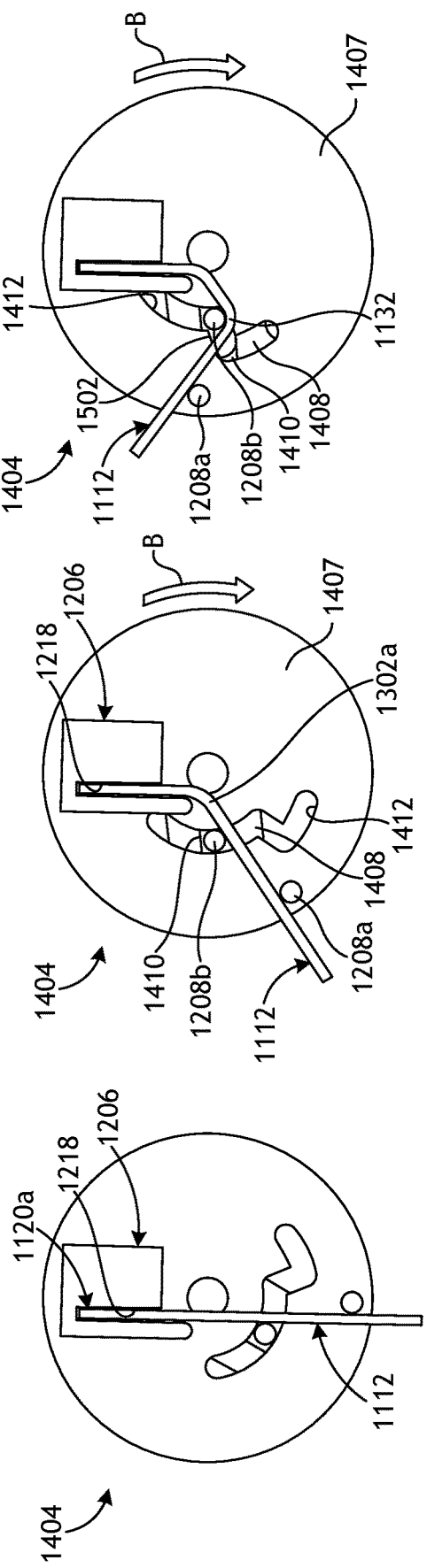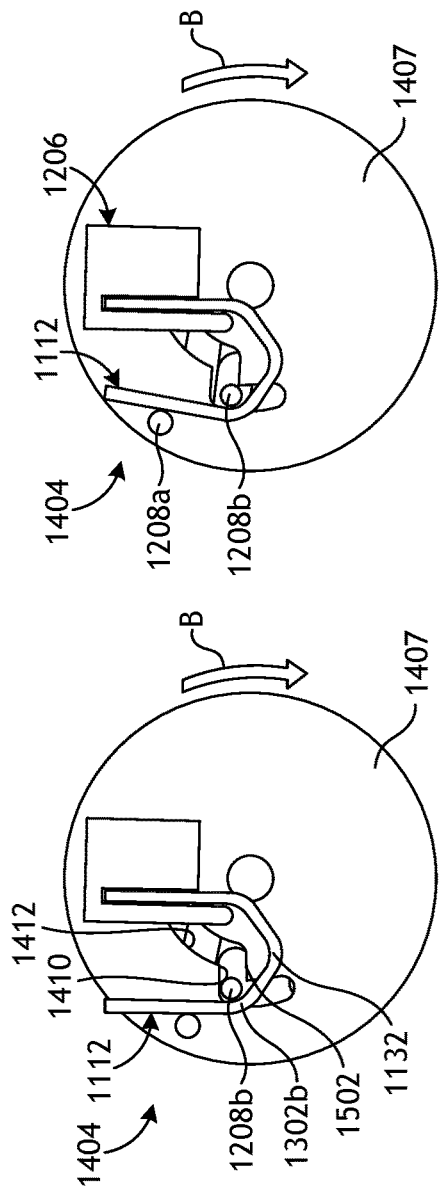

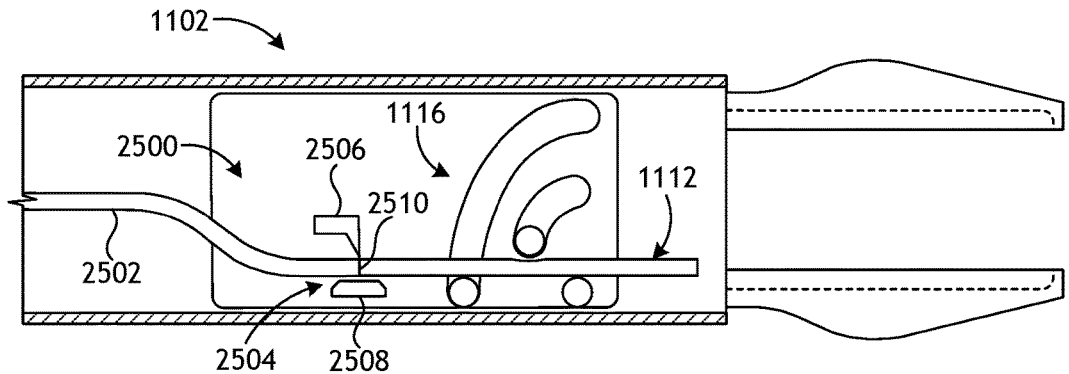
*FIG. 25A*
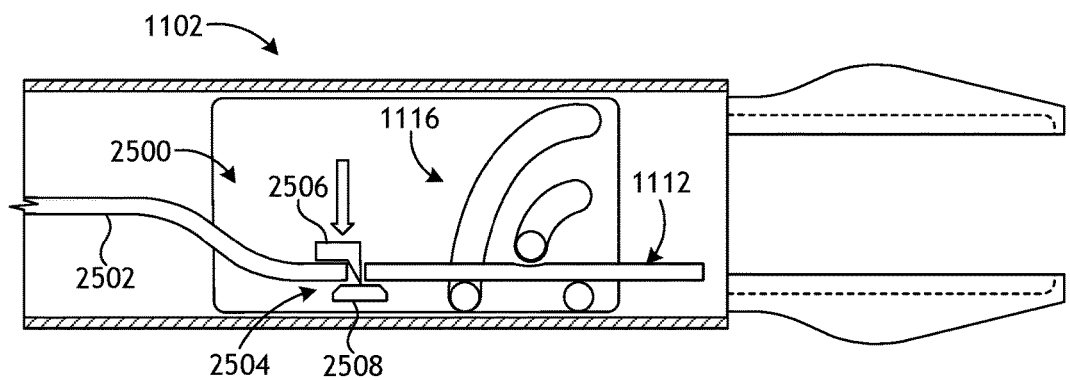
*FIG. 25B*
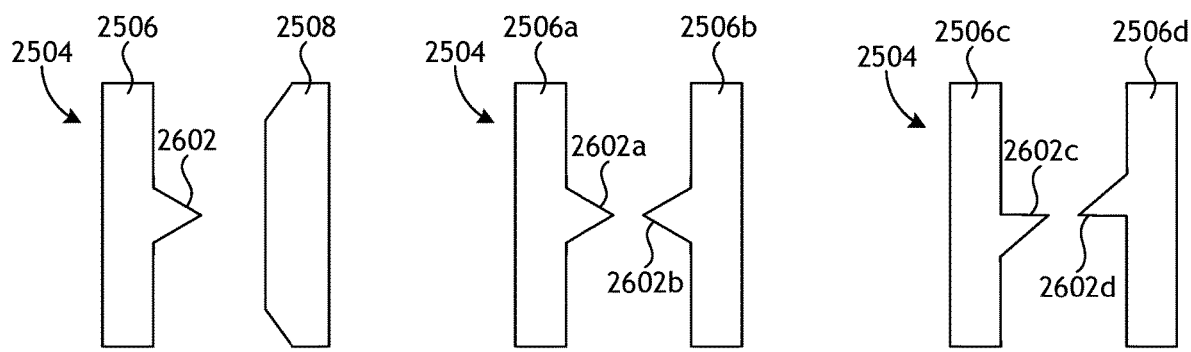
*FIG. 26A*  *FIG. 26B*  *FIG. 26C*

SURGICAL CLIP APPLIER WITH CLIP FORMING SYSTEM

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which a small incision is formed in the abdomen of a patient and a trocar is inserted through the incision to form a surgical access pathway for a surgical tool and elongate shaft. Once located within the abdomen, the surgical tool engages and/or treats tissue in a number of ways to achieve a diagnostic or therapeutic effect. Manipulation and engagement of the surgical tool may take place via various components passing through the elongate shaft.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical clip or "ligation clip" therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to manipulate and engage surgical instruments via an electronic interface communicatively coupled to a robotic manipulator. With the advances of robotic surgery, a user need not even be in the operating room with the patient during the surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 13A-13E are progressive top views of the clip forming system of FIGS. 12A and 12B showing example operation in bending a surgical clip into its tissue-ready state.

FIG. 14A is an exposed isometric view of another example end effector.

FIG. 14B is an isometric top view of the clip forming system of FIG. 14A.

FIG. 14C is an isometric bottom view of the clip forming system of FIGS. 14A and 14B.

FIGS. 15A-15E are progressive top views of the clip forming system of FIGS. 14A-14C showing example operation in bending a surgical clip into its tissue-ready state.

FIGS. 25A and 25B are progressive top views of another example clip feeding assembly for feeding unformed surgical clips into a clip forming system.

FIGS. 26A-26C depict alternate embodiments for the cutting system of FIGS. 25A-25B.

DETAILED DESCRIPTION

The present disclosure is related to surgical systems and, more particularly, to surgical clip appliers and related end effectors that include a surgical clip forming system capable of transitioning unformed surgical clips into tissue-ready surgical clips ready for crimping between opposed jaw members.

Embodiments discussed herein describe improvements to clip applier end effectors. The end effectors described herein include an elongate body, a clip forming system positioned within the body and arranged to receive an unformed surgical clip, and an actuation mechanism operatively coupled to the clip forming system to actuate the clip forming system and thereby bend the unformed surgical clip into a tissue-ready surgical clip. First and second jaw members are positioned at a distal end of the body and arranged to receive the tissue-ready surgical clip for crimping. The clip forming system can include a clip receiver feature arranged to receive a distal end of the unformed surgical clip, an apex stop feature engageable with the unformed surgical clip to help form a crown of the tissue-ready surgical clip, and a bending feature movable relative to the clip receiver feature and engageable with the unformed surgical clip to bend the unformed surgical clip into the tissue-ready surgical clip. Storing unformed surgical clips distal to an articulable wrist and forming the unformed surgical clips to tissue-ready surgical clips at the end effector may advantageously maximize the number of surgical clips with a minimized distal length past the articulation joint.

Figure 1:
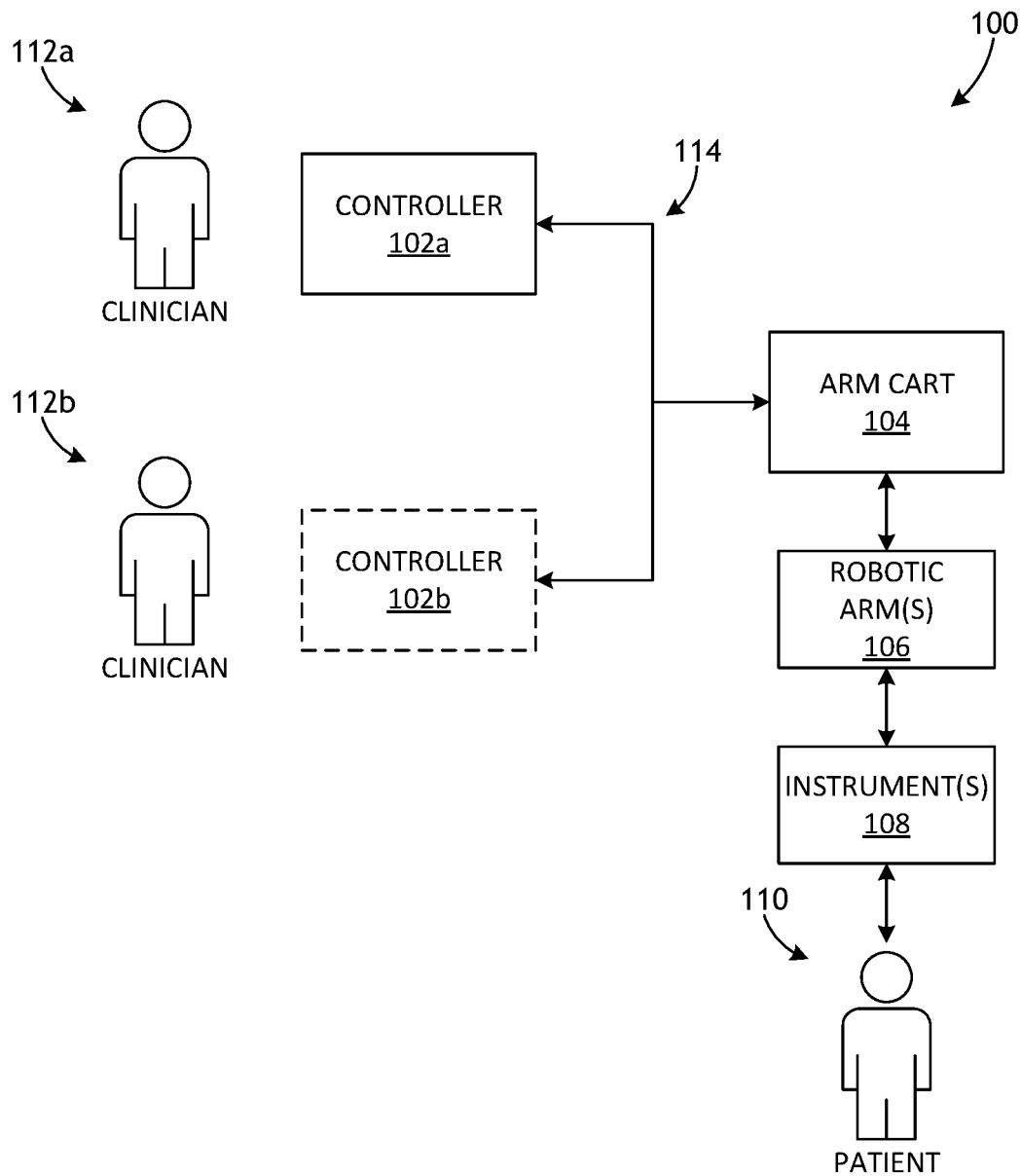
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
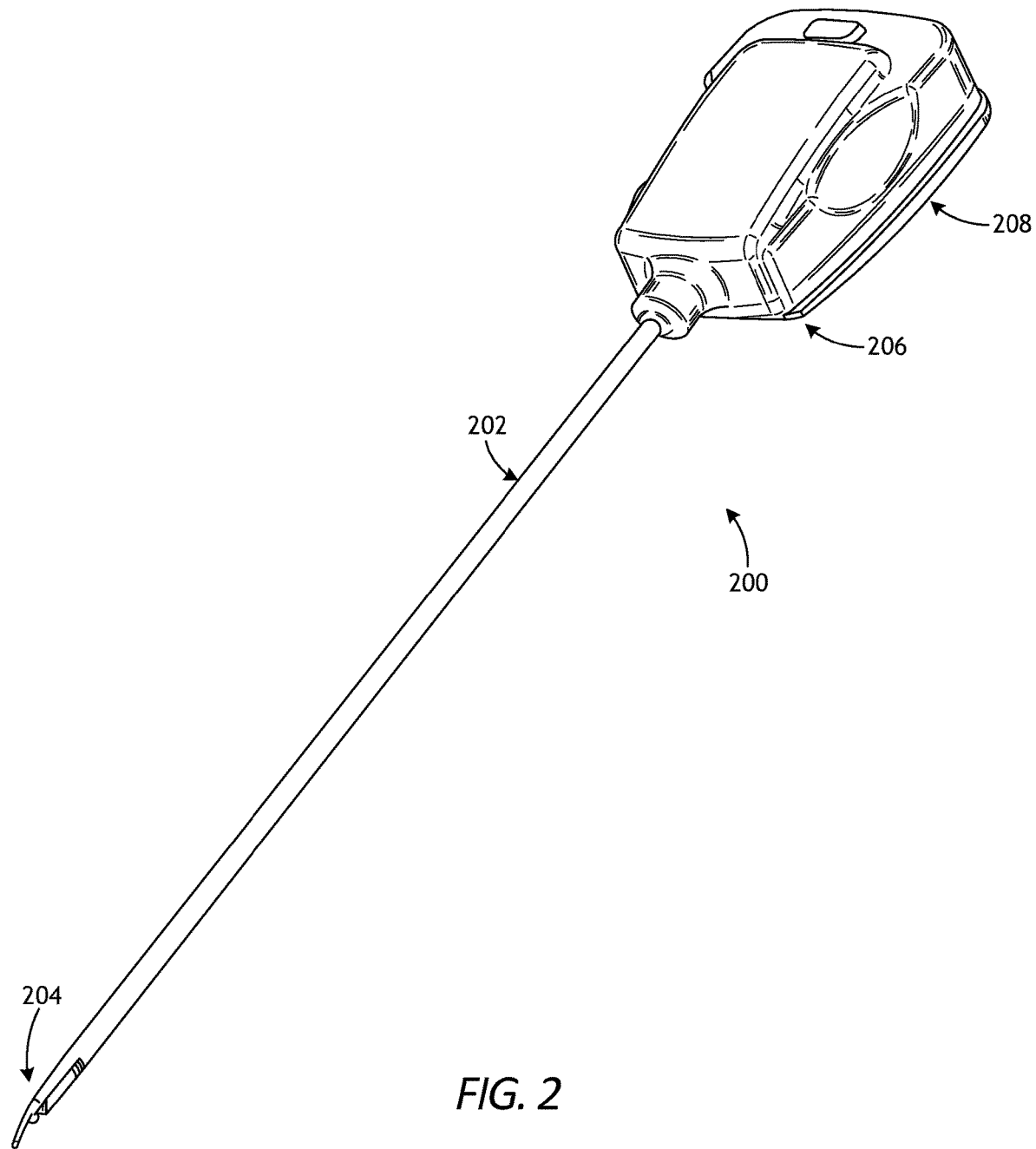
FIG. 2 is an isometric top view of an example surgical tool that may incorporate some or all of the principles of the present disclosure.

FIG. 2 is an isometric top view of an example surgical tool 200 that may incorporate some or all of the principles of the present disclosure. The surgical tool 200 may be the same as or similar to the surgical instrument(s) 108 of FIG. 1 and, therefore, may be used in conjunction with the robotic surgical system 100 of FIG. 1. Accordingly, the surgical tool 200 may be designed to be releasably coupled to a robotic arm 106 (FIG. 1) of a robotic manipulator of the robotic surgical system 100. Full detail and operational description of the surgical tool 200 is provided in U.S. Patent Pub. 2016/0287252, entitled "Clip Applier Adapted for Use with a Surgical Robot," the contents of which are hereby incorporated by reference in their entirety.

While the surgical tool 200 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 200 can include an elongate shaft 202, an end effector 204 coupled to the distal end of the shaft 202, and a drive housing 206 coupled to the proximal end of the shaft 202. The terms "proximal" and "distal" are defined herein relative to a robotic surgical system having an interface configured to mechanically and electrically couple the surgical tool 200 (e.g., the drive housing 206) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

In applications where the surgical tool 200 is used in conjunction with a robotic surgical system (e.g., system 100 of FIG. 1), the drive housing 206 can include a tool mounting portion 208 designed with features that releasably couple the surgical tool 200 to a robotic arm (e.g., the robotic arms 106 or "tool drivers" of FIG. 1) of a robotic manipulator. The tool mounting portion 208 may releasably attach (couple) the drive housing 206 to a tool driver in a variety of ways, such as by clamping thereto, clipping thereto, or slidably mating therewith. In some embodiments, the tool mounting portion 208 may include an array of electrical connecting pins, which may be coupled to an electrical connection on the mounting surface of the tool driver. While the tool mounting portion 208 is described herein with reference to mechanical, electrical, and magnetic coupling elements, it should be understood that a wide variety of telemetry modalities might be used, including infrared, inductive coupling, or the like.

Figure 3:
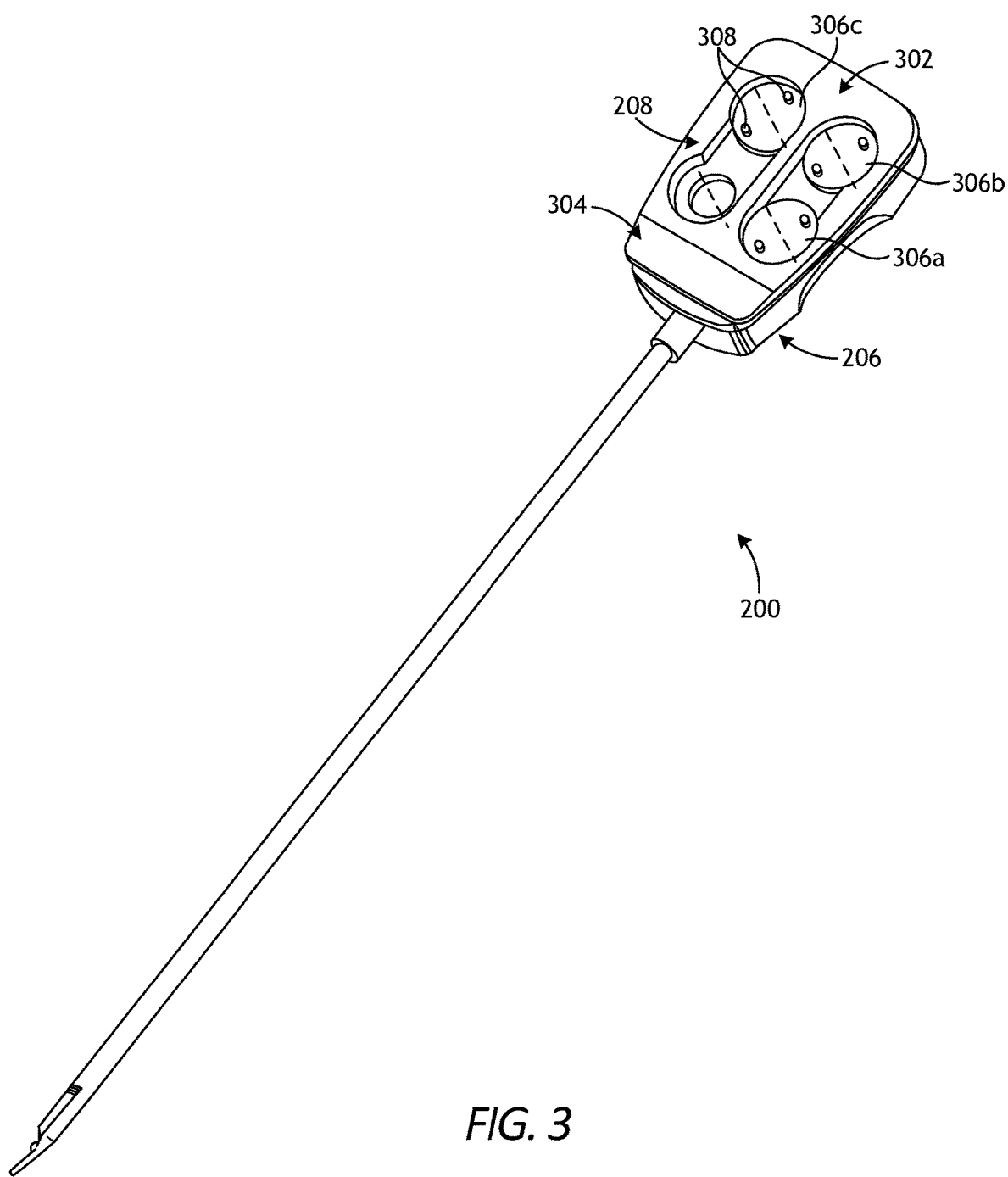
FIG. 3 is an isometric bottom view of the surgical tool of FIG. 2.

FIG. 3 is an isometric bottom view of the surgical tool 200. The surgical tool 200 further includes an interface 302 that mechanically and electrically couples the tool mounting portion 208 to a robotic manipulator. In various embodiments, the tool mounting portion 208 includes a tool mounting plate 304 that operably supports a plurality of drive inputs, shown as a first drive input 306a, a second drive input 306b, and a third drive input 306c. While only three drive inputs 306a-c are shown in FIG. 3, more or less than three may be employed, without departing from the scope of the disclosure.

In the illustrated embodiment, each drive input 306a-c comprises a rotatable disc configured to align with and couple to a corresponding input actuator (not shown) of a given tool driver. Moreover, each drive input 306a-c provides or defines one or more surface features 308 configured to align with mating surface features provided on the corresponding input actuator. The surface features 308 can include, for example, various protrusions and/or indentations that facilitate a mating engagement.

Figure 4:
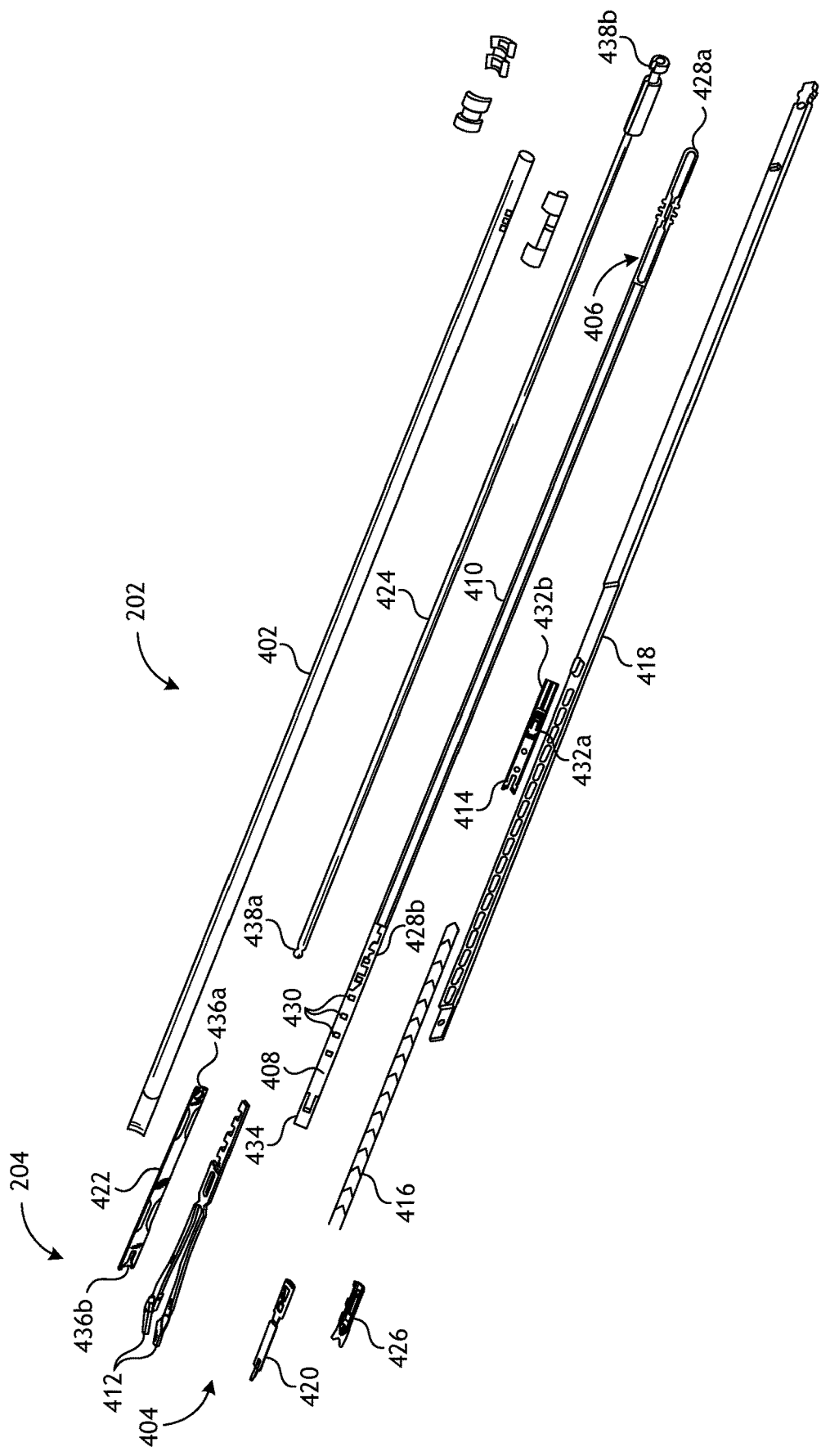
FIG. 4 is an exploded view of the elongate shaft and the end effector of the surgical tool of FIGS. 2 and 3.

FIG. 4 is an exploded view of one example of the elongate shaft 202 and the end effector 204 of the surgical tool 200 of FIGS. 2 and 3, according to one or more embodiments. As illustrated, the shaft 202 includes an outer tube 402 that houses the various components of the shaft 202, which can include a jaw retaining assembly 404. The jaw retaining assembly 404 includes a jaw retainer shaft 406 with a clip track 408 and a push rod channel 410 formed thereon. The end effector 204 includes opposing jaws 412 that are configured to mate to a distal end of the clip track 408.

The shaft 202 also includes a clip advancing assembly, which, in one example embodiment, can include a feeder shoe 414 adapted to be slidably disposed within the clip track 408. The feeder shoe 414 is designed to advance a series of clips 416 positioned within the clip track 408, and a feedbar 418 is adapted to drive the feeder shoe 414 through the clip track 408. An advancer assembly 420 is adapted to mate to a distal end of the feedbar 418 for advancing a distal-most clip into the jaws 412.

The shaft 202 further includes a clip forming or camming assembly operable to collapse the jaws 412 and thereby crimp (crush) a surgical clip 416 positioned between (interposing) the jaws 412. The camming assembly includes a cam 422 that slidably mates to the jaws 412, and a push rod 424 that moves the cam 422 relative to the jaws 412 to collapse the jaws 412. A tissue stop 426 can mate to a distal end of the clip track 408 to help position the jaws 412 relative to a surgical site.

The jaw retainer shaft 406 is extendable within and couples to the outer tube 402 at a proximal end 428a, and its distal end 428b is adapted to mate with the jaws 412. The push rod channel 410 formed on the jaw retainer shaft 406 may be configured to slidably receive the push rod 424, which is used to advance the cam 422 over the jaws 412. The clip track 408 extends distally beyond the distal end 428b of the jaw retainer shaft 406 to allow a distal end of the clip track 408 to be substantially aligned with the jaws 412.

The clip track 408 can include several openings 430 formed therein for receiving an upper or "superior" tang 432a formed on the feeder shoe 414 adapted to be disposed within the clip track 408. The clip track 408 can also include a stop tang 434 formed thereon that is effective to be engaged by a corresponding stop tang formed on the feeder shoe 414 to prevent movement of the feeder shoe 414 beyond a distal-most position. To facilitate proximal movement of the feeder shoe 414 within the clip track 408, the feeder shoe 414 can also include a lower or "inferior" tang 432b formed on the underside thereof for allowing the feeder shoe 414 to be engaged by the feedbar 418 as the feedbar 418 is moved distally. In use, each time the feedbar 418 is moved distally, a detent formed in the feedbar 418 engages the inferior tang 432b and moves the feeder shoe 414 distally a predetermined distance within the clip track 408. The feedbar 418 can then be moved proximally to return to its initial position, and the angle of the inferior tang 432b allows the inferior tang 432b to slide into the next detent formed in the feedbar 418.

The jaws 412 include first and second opposed jaw members that are movable (collapsible) relative to one another and are configured to receive a surgical clip from the series of clips 416 therebetween. The jaw members can each include a groove formed on opposed inner surfaces thereof for receiving the legs of a surgical clip 416 in alignment with the jaw members. In the illustrated embodiment, the jaw members are biased to an open position and a force is required to urge the jaw members toward one another to crimp the interposing clip 416. The jaw members can also each include a cam track formed thereon for allowing the cam 422 to slidably engage and move the jaw members toward one another. A proximal end 436a of the cam 422 is matable with a distal end 438a of the push rod 424, and a distal end 436b of the cam 422 is adapted to engage and actuate the jaws 412. The proximal end 438b of the push rod 424 is matable with a closure link assembly associated with the drive housing 206 for moving the push rod 424 and the cam 422 relative to the jaws 412.

The distal end 436b of the cam 422 includes a camming channel or tapering recess formed therein for slidably receiving corresponding cam tracks provided by the jaw members. In operation, the cam 422 is advanced from a proximal position, in which the jaw members are spaced apart from one another, to a distal position, where the jaw members are collapsed to a closed position. As the cam 422 is advanced over the jaw members, the tapering recess at the distal end 436b serves to push the jaw members toward one another, thereby crimping a surgical clip 416 disposed therebetween.

Figure 5:
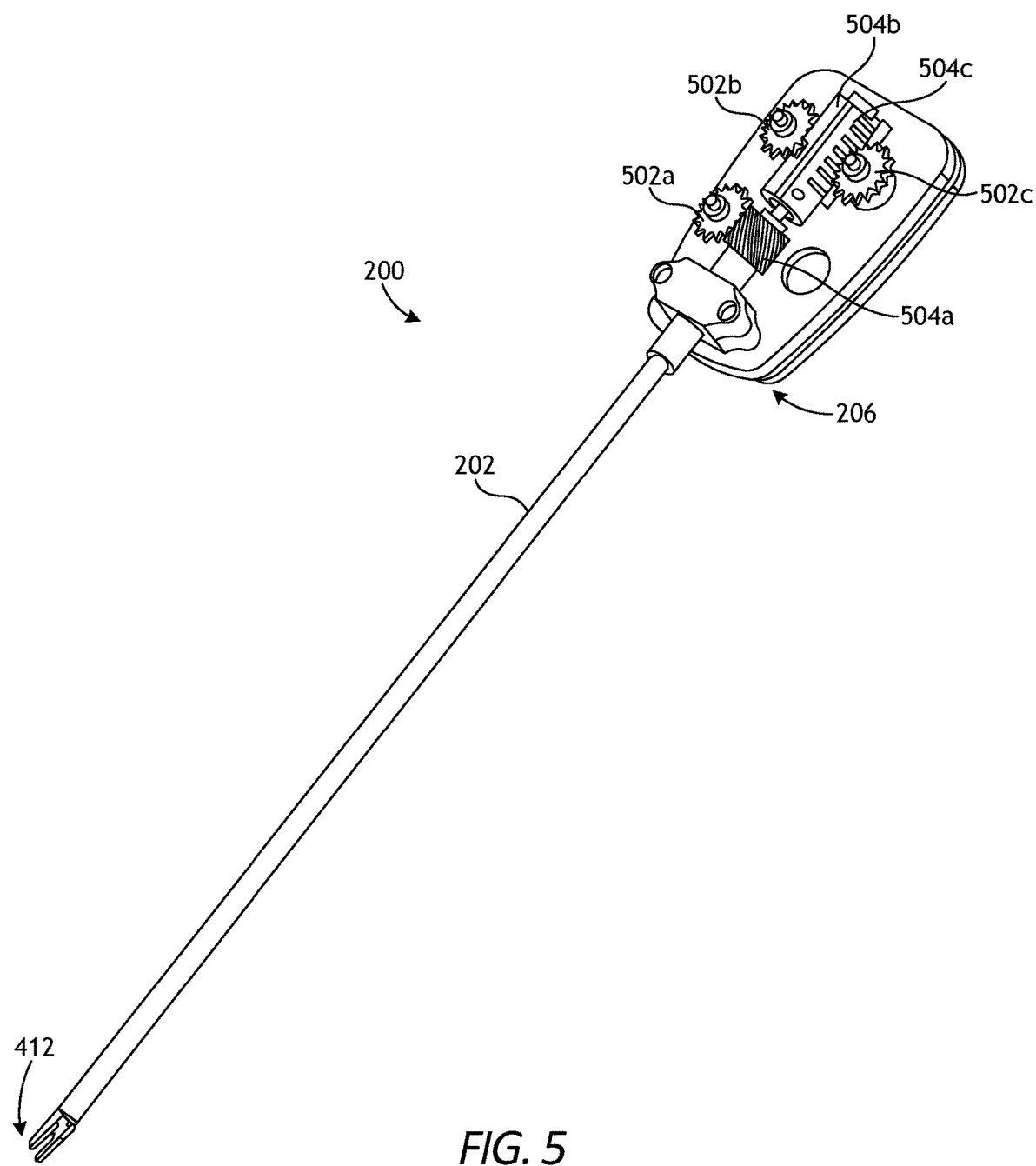
FIG. 5 is an exposed isometric view of the surgical tool of FIG. 2.

FIG. 5 is an exposed isometric view of the surgical tool 200 of FIG. 2, according to one or more embodiments. The shroud or covering of the drive housing 206 has been removed to reveal the internal component parts. As illustrated, the surgical tool 200 may include a first drive gear 502a, a second drive gear 502b, and a third drive gear 502c. The first drive gear 502a may be operatively coupled to (or extend from) the first drive input 306a (FIG. 3) such that actuation of the first drive input 306a correspondingly rotates the first drive gear 502a. Similarly, the second and third drive gears 502b,c may be operatively coupled to (or extend from) the second and third drive inputs 306b,c (FIG. 3), respectively, such that actuation of the second and third drive inputs 306b,c correspondingly rotates the second and third drive gears 502b,c, respectively.

The first drive gear 502a may be configured to intermesh with a first driven gear 504a, which is operatively coupled to the shaft 202. In the illustrated embodiment, the driven gear 504a comprises a helical gear. In operation, rotation of the first drive gear 502a about a first axis correspondingly rotates the first driven gear 504a about a second axis orthogonal to the first axis to control rotation of the shaft 202 in clockwise and counter-clockwise directions based on the rotational direction of the first drive gear 502a.

The second drive gear 502b may be configured to intermesh with a second driven gear 504b (partially visible in FIG. 5), and the third drive gear 502c may be configured to intermesh with a third driven gear 504c. In the illustrated embodiment, the second and third drive and driven gears 502b,c, 504b,c comprise corresponding rack and pinion interfaces, where the driven gears 504b,c comprise the rack and the drive gears 502b,c comprise the pinion. Independent rotation of the second and third drive gears 502b,c will cause the second and third driven gears 504b,c, respectively, to translate linearly relative to (independent of) one another.

In at least one embodiment, actuation (rotation) of the third drive gear 502c will result in a surgical clip 416 (FIG. 4) being fed into the jaws 412. More particularly, the third driven gear 504c may be operatively coupled to the feedbar 418 (FIG. 4) and, upon rotation of the third drive gear 502c in a first angular direction, the third driven gear 504c will advance distally and correspondingly advance the feedbar 418 a sufficient distance to fully advance a surgical clip into the jaws 412. Rotation of the third drive gear 502c may be precisely controlled by an electrical and software interface to deliver the exact linear travel to the third driven gear 504c necessary to feed a clip 416 into the jaws 412.

Upon delivery of a clip into the jaws 412, or after a predetermined amount of rotation of the third drive gear 502c, rotation of the third drive gear 502c is reversed in a second angular direction to move the third driven gear 504c linearly in a proximal direction, which correspondingly moves the feedbar 418 proximally. This process may be repeated several times to accommodate a predetermined number of clips residing in the shaft 202.

Actuation of the second drive gear 502b causes the jaws 412 to close or collapse to crimp a surgical clip. More particularly, the second driven gear 504b may be coupled to the proximal end 438b (FIG. 4) of the push rod 424 (FIG. 4) and, upon actuation of the second drive gear 502b in a first angular direction, the second driven gear 504b will be advanced linearly in a distal direction and correspondingly drive the push rod 424 distally, which drives the cam 422 over the jaws 412 to collapse the jaw members and crimp a surgical clip positioned in the jaws 412. Once a surgical clip is successfully deployed, rotation of the second drive gear 502b is reversed in the opposite angular direction to move the second driven gear 504b in a proximal direction, which correspondingly moves the push rod 424 and the cam 422 proximally and permits the jaws 412 to open once again.

The processes of delivering a surgical clip into the jaws 412 and collapsing the jaws 412 to crimp the surgical clip are not limited to the actuation mechanisms and structures described herein. In alternative embodiments, for example, the second and third driven gears 504b,c may instead comprise capstan pulleys configured to route and translate drive cables within the shaft 202. In such embodiments, the drive cables may be operatively coupled to one or more lead screws or other types of rotating members positioned within the shaft 202 near the distal end and capable of advancing the feedbar 418 to deliver a surgical clip into the jaws 412 and advancing the cam 422 to collapse the jaws 412 and crimp the surgical clip.

Figure 6:
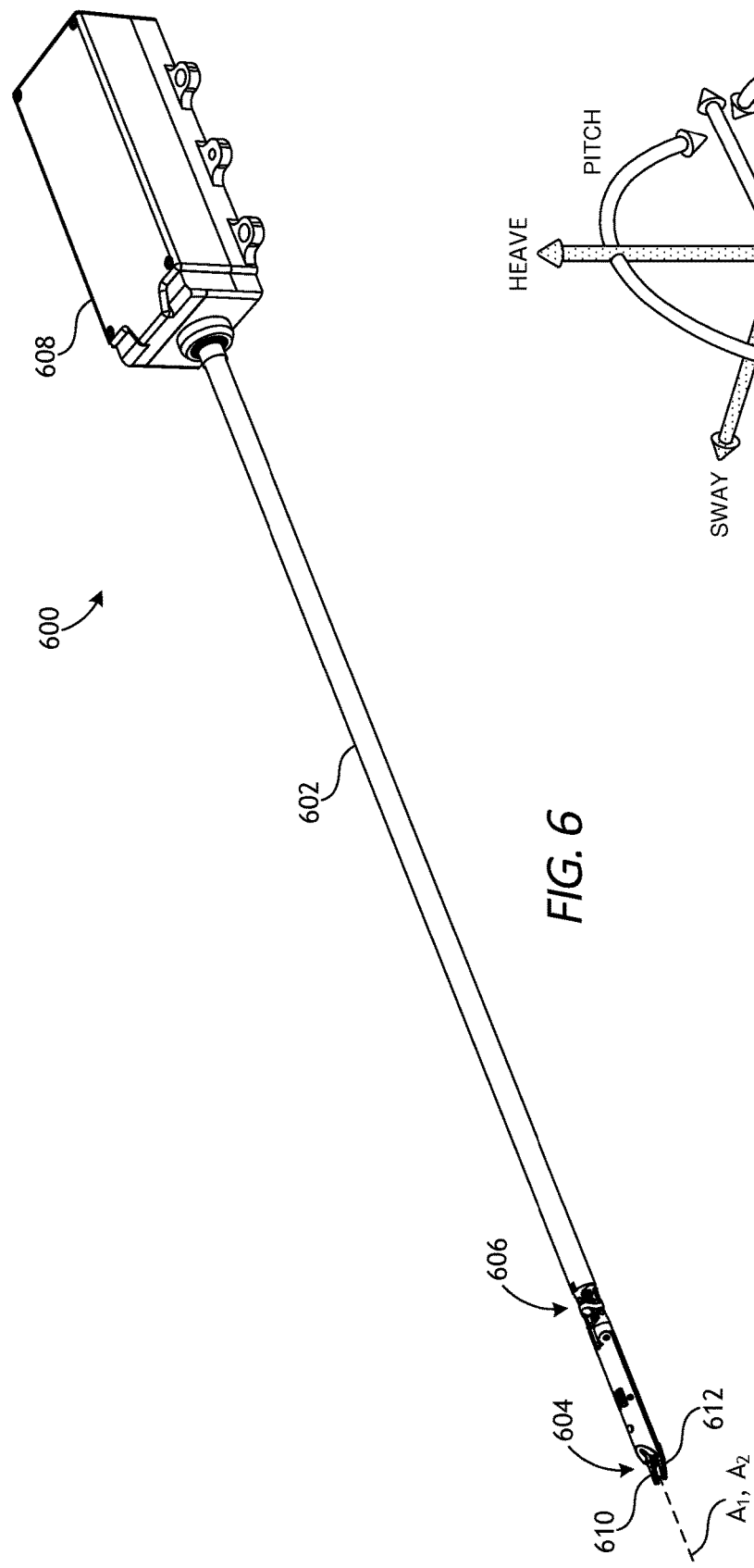
FIG. 6 is a side view of an example surgical tool that may incorporate some or all of the principles of the present disclosure.

FIG. 6 is an isometric top view of another example surgical tool 600 that may incorporate some or all of the principles of the present disclosure. Similar to the surgical tool 200 of FIG. 2, the surgical tool 600 may be used in conjunction with the robotic surgical system 100 of FIG. 1. As illustrated, the surgical tool 600 includes an elongate shaft 602, an end effector 604 positioned at the distal end of the shaft 602, a wrist 606 (alternately referred to as a "articulable wrist joint") that couples the end effector 604 to the distal end of the shaft 602, and a drive housing 608 coupled to the proximal end of the shaft 602. In some embodiments, the shaft 602, and hence the end effector 604 coupled thereto, is configured to rotate about a longitudinal axis $A_1$.

In the illustrated embodiment, the end effector 604 comprises a clip applier that includes opposing jaw members 610, 612 configured to collapse toward one another to crimp a surgical clip. The wrist 606 comprises an articulatable joint that facilitates pivoting movement of the end effector 604 relative to the shaft 602 to position the end effector 604 at desired orientations and locations relative to a surgical site. The housing 608 includes (contains) various actuation mechanisms designed to control articulation and operation of the end effector 604.

Figure 7:
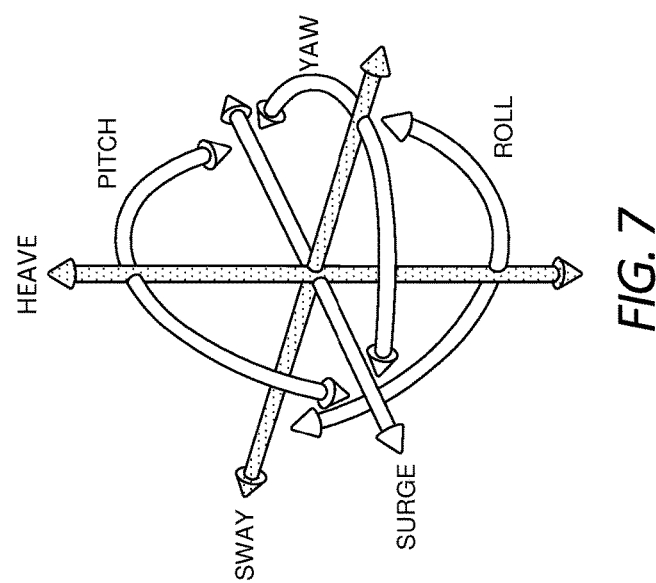
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 includes a plurality of drive cables (generally obscured in FIG. 6) that form part of a cable driven motion system configured to facilitate operation and articulation (movement) of the end effector 604 relative to the shaft 602. For example, selectively moving the drive cables can actuate the end effector 604 and thereby collapse the jaw members 610, 612 toward each other. Moreover, moving the drive cables can also move the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. In the articulated position, the longitudinal axes $A_1$, $A_2$ would be angularly offset from each other such that the end effector 604 is at a non-zero angle relative to the shaft 602.

Figure 8:
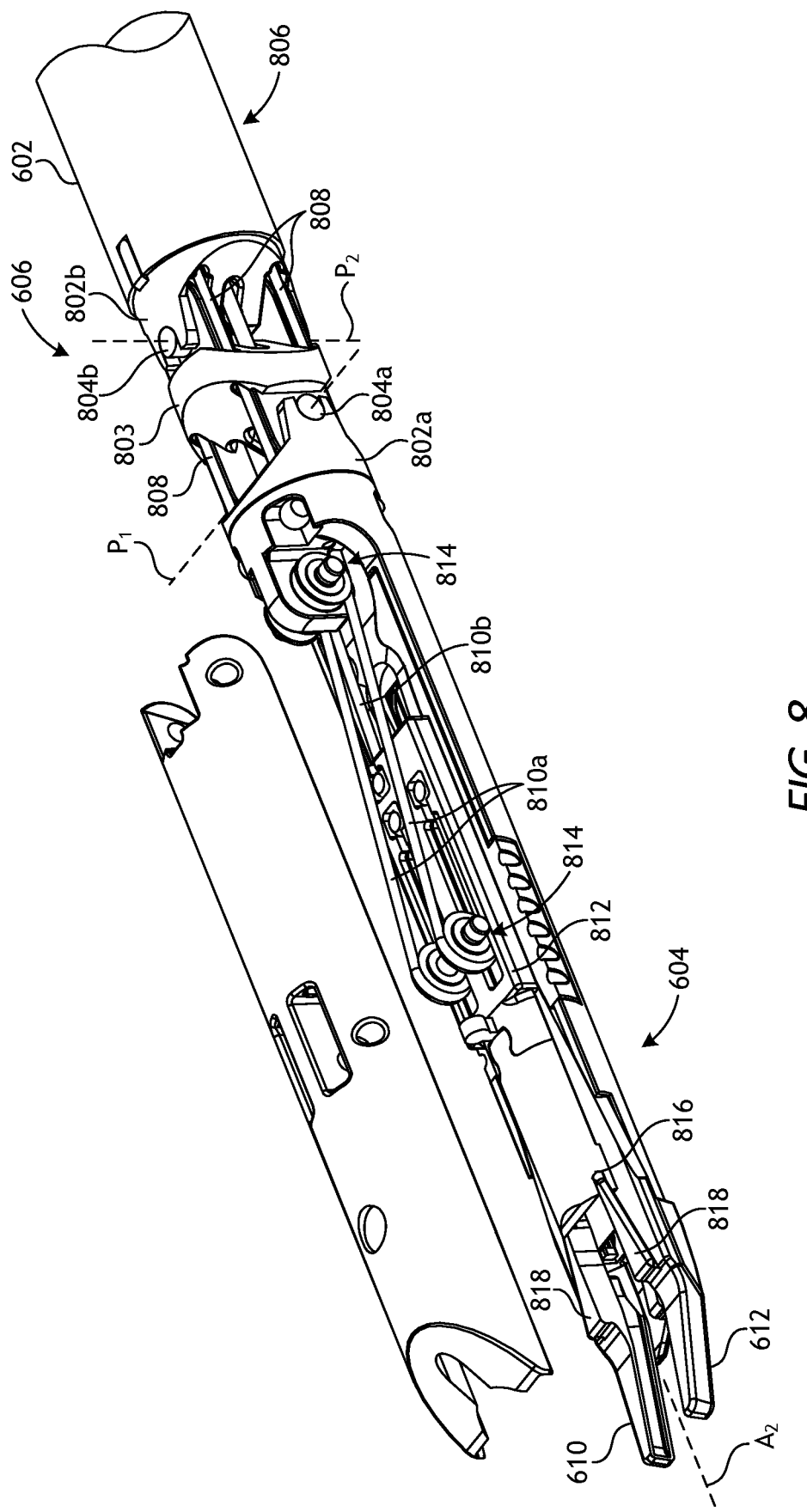
FIG. 8 is an enlarged isometric view of the distal end of the surgical tool of FIG. 6.

FIG. 8 is an enlarged isometric view of the distal end of the surgical tool 600 of FIG. 6. More specifically, FIG. 8 depicts an enlarged and partially exploded view of the end effector 604 and the wrist 606. The wrist 606 operatively couples the end effector 604 to the shaft 602. To accomplish this, the wrist 606 includes a distal clevis 802a, a proximal clevis 802b, and a spacer 803 interposing the distal and proximal clevises 802a,b. The end effector 604 is coupled to the distal clevis 802a and the distal clevis 802a is rotatably mounted to the spacer 803 at a first axle 804a. The spacer 803 is rotatably mounted to the proximal clevis 802b at a second axle 804b and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "pitch" articulation of the end effector 604, and movement about the second pivot axis $P_2$ provides "yaw" articulation of the end effector 604.

A plurality of drive cables 808 extend longitudinally within the shaft 602 and pass through the wrist 606 to be operatively coupled to the end effector 604. The drive cables 808 form part of the cable driven motion system briefly described above, and may be referred to and otherwise characterized as cables, bands, lines, cords, wires, ropes, strings, twisted strings, elongate members, etc. The drive cables 808 can be made from a variety of materials including, but not limited to, metal (e.g., tungsten, stainless steel, etc.) or a polymer.

The drive cables 808 extend proximally from the end effector 604 to the drive housing 608 (FIG. 6) where they are operatively coupled to various actuation mechanisms or devices housed (contained) therein to facilitate longitudinal movement (translation) of the drive cables 808. Selective actuation of the drive cables 808 causes the end effector 604 to articulate (pivot) relative to the shaft 602. Moving a given drive cable 808 constitutes applying tension (i.e., pull force) to the given drive cable 808 in a proximal direction, which causes the given drive cable 808 to translate and thereby cause the end effector 604 to move (articulate) relative to the shaft 602.

One or more actuation cables 810, shown as first actuation cables 810a and second actuation cables 810b, may also extend longitudinally within the shaft 602 and pass through the wrist 606 to be operatively coupled to the end effector 604. The actuation cables 810a,b may be similar to the drive cables 808 and also form part of the cable driven motion system. Selectively actuating the actuation cables 810a,b causes the end effector 604 to actuate, such as collapsing the first and second jaw members 610, 612 to crimp a surgical clip (not shown).

More specifically, the actuation cables 810a,b may be operatively coupled to a cam 812 that is slidably engageable with the jaw members 610, 612. One or more pulleys 814 may be used to receive and redirect the first actuation cables 810a for engagement with the cam 812. Longitudinal movement of the first actuation cables 810a correspondingly moves the cam 812 distally relative to the jaw members 610, 612. The distal end of the cam 812 includes a tapering recess or camming channel 1204 formed therein for slidably receiving corresponding cam tracks 818 provided by the jaw members 610, 612. As the cam 812 is advanced distally, the camming channel 1204 pushes (collapses) the jaw members 610, 612 toward one another, thereby crimping a surgical clip (not shown) disposed therebetween. Actuation of the second actuation cables 810b (one shown) pulls the cam 812 proximally, thereby allowing the jaw members 610, 612 to open again to receive another surgical clip.

Although not expressly depicted in FIG. 8, an assembly including, for example, a feedbar, a feeder shoe, and a clip track may be included at or near the end effector 604 to facilitate feeding surgical clips into the jaw members 610, 612. In some embodiments, the feedbar (or a connecting member) may be flexible and extend through the wrist 606.

Figure 9:
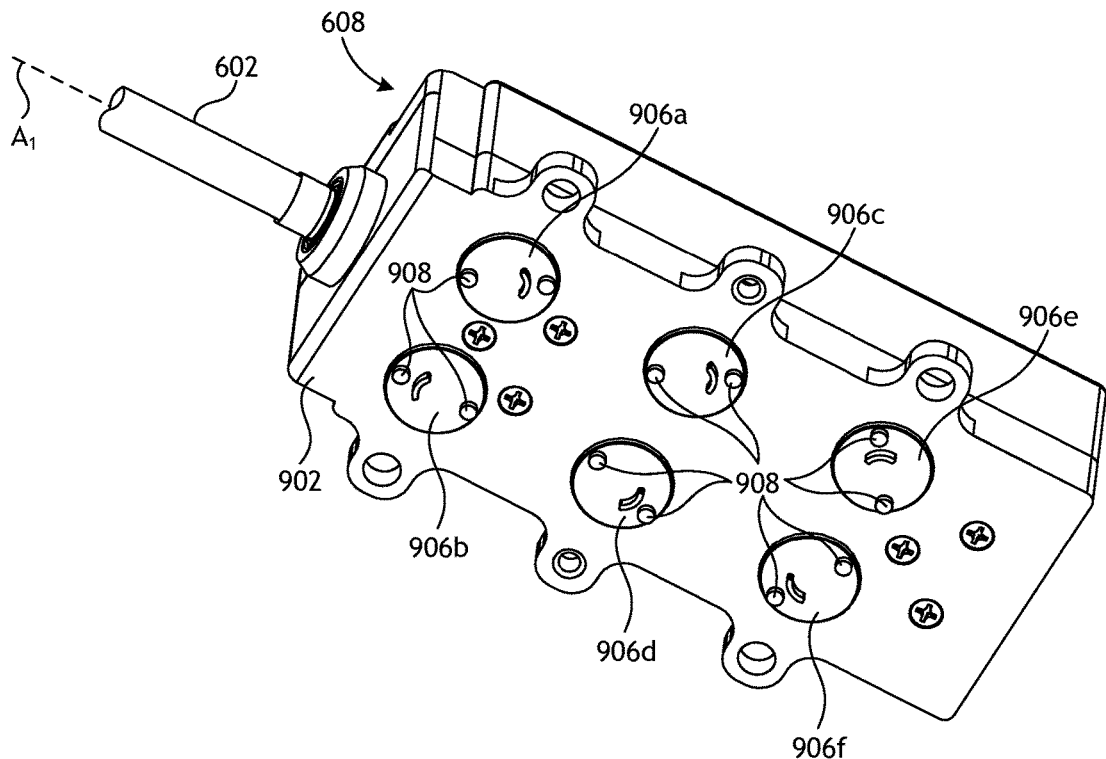
FIG. 9 is a bottom view of the drive housing of the surgical tool of FIG. 6.

FIG. 9 is a bottom view of the drive housing 608, according to one or more embodiments. As illustrated, the drive housing 608 may include a tool mounting interface 902 used to operatively couple the drive housing 608 to a tool driver of a robotic manipulator. The tool mounting interface 902 may mechanically, magnetically, and/or electrically couple the drive housing 608 to a tool driver.

As illustrated, the interface 902 includes and supports a plurality of drive inputs, shown as drive inputs 906a, 906b, 906c, 906d, 906e, and 906f. Each drive input 906a-f may comprise a rotatable disc configured to align with and couple to a corresponding input actuator (not shown) of a tool driver. Moreover, each drive input 906a-f provides or defines one or more surface features 908 configured to align with mating features provided on the corresponding input actuator. The surface features 908 can include, for example, various protrusions and/or indentations that facilitate a mating engagement.

In some embodiments, actuation of the first drive input 906a may control rotation of the elongate shaft 602 about its longitudinal axis $A_1$. Depending on the rotational actuation of the first drive input 906a, the elongate shaft 602 may be rotated clockwise or counter-clockwise. In some embodiments, selective actuation of the second and third drive inputs 906b,c may cause movement (axial translation) of the actuation cables 810a,b (FIG. 8), which causes the cam 812 (FIG. 8) to move and crimp a surgical clip, as generally described above. In some embodiments, actuation of the fourth drive input 906d feeds a surgical clip into the jaw members 610, 612 (FIG. 8). In some embodiments, actuation of the fifth and sixth drive inputs 906e,f causes movement (axial translation) of the drive cables 808 (FIG. 8), which results in articulation of the end effector 604. Each of the drive inputs 906a-f may be actuated based on user inputs communicated to a tool driver coupled to the interface 902, and the user inputs may be received via a computer system incorporated into the robotic surgical system.

Figure 10:
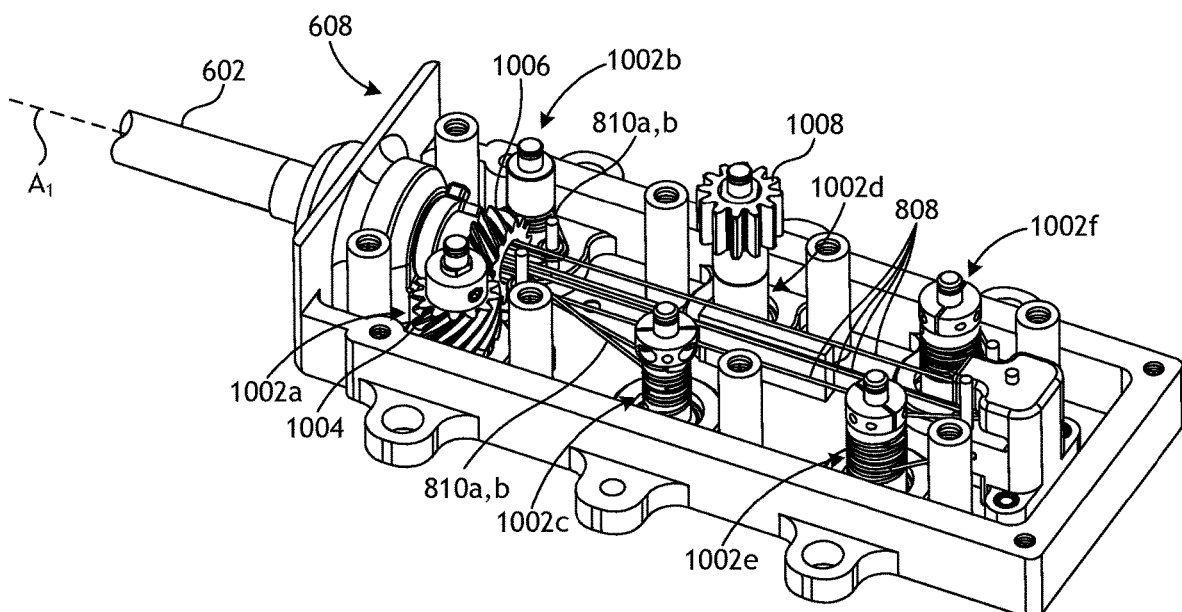
FIG. 10 is an isometric exposed view of the interior of the drive housing of the surgical tool of FIG. 6.

FIG. 10 is an isometric exposed view of the interior of the drive housing 608, according to one or more embodiments. Several component parts that may otherwise be contained within the drive housing 608 are not shown in FIG. 10 to enable discussion of the depicted component parts.

As illustrated, the drive housing 608 contains a first capstan 1002a, which is operatively coupled to or extends from the first drive input 906a (FIG. 9) such that actuation of the first drive input 906a results in rotation of the first capstan 1002a. A helical drive gear 1004 is coupled to or forms part of the first capstan 1002a and is configured to mesh and interact with a driven gear 1006 operatively coupled to the shaft 602 such that rotation of the driven gear 1006 correspondingly rotates the shaft 602. Accordingly, rotation of the helical drive gear 1004 (via actuation of the first drive input 906a of FIG. 9) will drive the driven gear 1006 and thereby control rotation of the elongate shaft 602 about the longitudinal axis $A_1$.

The drive housing 608 also includes second and third capstans 1002b and 1002c operatively coupled to or extending from the second and third drive inputs 906b,c (FIG. 9), respectively, such that actuation of the second and third drive inputs 906b,c results in rotation of the second and third capstans 1002b,c. The second and third capstans 1002b,c comprise capstan pulleys operatively coupled to the actuation cables 810a,b (FIG. 8) such that rotation of a given capstan 1002b,c actuates (longitudinally moves) a corresponding one of the actuation cables 810a,b. Accordingly, selective rotation of the second and third capstans 1002b,c via actuation of the second and third drive inputs 906b,c, respectively, will cause movement (axial translation) of the actuation cables 810a,b, which causes the cam 812 (FIG. 8) to move and crimp a surgical clip.

The drive housing 608 further includes a fourth capstan 1002d, which is operatively coupled to or extends from the fourth drive input 906d (FIG. 9) such that actuation of the fourth drive input 906d results in rotation of the fourth capstan 1002d. A spur gear 1008 is coupled to or forms part of the fourth capstan 1002d and is configured to mesh and interact with a rack gear (not shown) also contained within the drive housing 608. The rack gear may be operatively coupled to a feedbar (or another connecting member) which facilitates operation of a feeder shoe and associated clip track to feed surgical clips into the jaw members 610, 612 (FIGS. 6 and 8). Accordingly, rotation of the spur gear 1008 (via actuation of the fourth drive input 906d) will control the feedbar and thereby control loading of surgical clips into the jaw members 610, 612 as desired.

The drive housing 608 further contains or houses fifth and sixth capstans 1002e and 1002f operatively coupled to or extending from the fifth and sixth drive inputs 906e,f (FIG. 9), respectively, such that actuation of the fifth and sixth drive inputs 906e,f results in rotation of the fifth and sixth capstans 1002e,f. The fifth and sixth capstans 1002e,f comprise capstan pulleys operatively coupled to the drive cables 808 (FIG. 8) such that rotation of a given capstan 1002e,f actuates (longitudinally moves) a corresponding one of the actuation cables 808. Accordingly, selective rotation of the fifth and sixth capstans 1002e,f via actuation of the fifth and sixth drive inputs 906e,f, respectively, will cause movement (axial translation) of the drive cables 808 and thereby articulate (pivot) the end effector 604 relative to the shaft 602.

The surgical tools 200, 600 described herein above may incorporate and facilitate the principles of the present disclosure in improving feeding and/or forming of surgical clips in robotic or non-robotic clip appliers. Moreover, it is contemplated herein to combine some or all of the features of the surgical tools 200, 600 to facilitate operation of the embodiments described below. Accordingly, example surgical tools that may incorporate the principles of the present disclosure may include geared actuators, capstan pulley and cable actuators, or any combination thereof, without departing from the scope of the disclosure.

FIGS. 11A-11D are partial cross-sectional top views of a distal portion of an example end effector 1102, according to one or more embodiments of the present disclosure. The end effector 1102 may be similar in some respects to the end effectors 204 and 604 of FIGS. 2 and 6, respectively. For instance, similar to the end effectors 204, 604, the end effector 1102 may be incorporated into either or both of the surgical tools 200, 600 described herein above. Moreover, the end effector 1102 may comprise a clip applier having opposed jaw members 1104 and 1106 actuatable to collapse toward one another to crimp a surgical clip. As described herein, the end effector 1102 may incorporate various component parts and actuatable mechanisms or features that facilitate the forming of surgical clips within the end effector 1102, feeding the formed surgical clips into the jaw members 1104, 1106, and collapsing the jaw members 1104, 1106 to crimp the formed surgical clips when desired.

FIGS. 11A-11D illustrate progressive views of the end effector 1102 during example operation of forming and feeding surgical clips into the jaw members 1104, 1106.

Figure 11A:
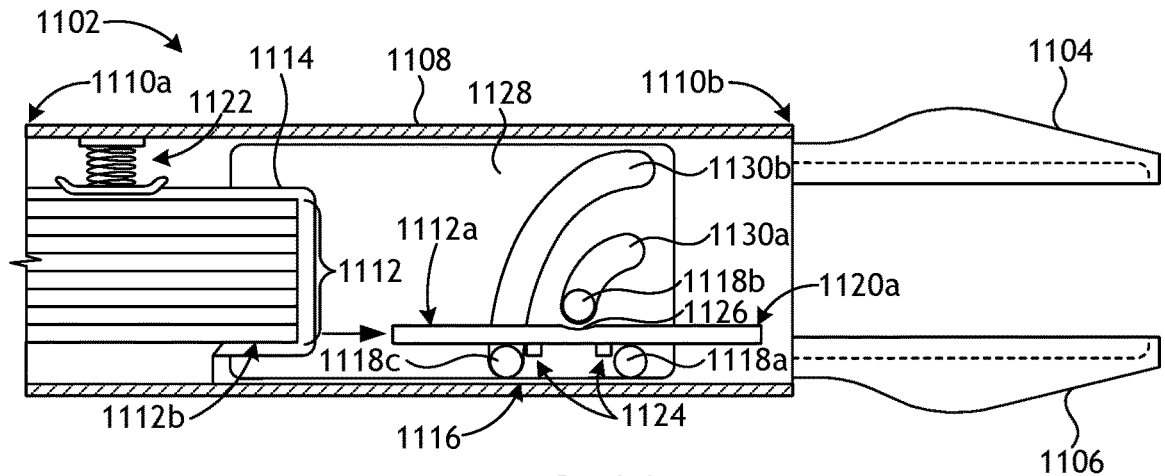
FIGS. 11A-11D are partial cross-sectional top views of a distal portion of an example end effector.

Referring first to FIG. 11A, the end effector 1102 includes an elongate body 1108 having a proximal end 1110a and a distal end 1110b. In some embodiments, the body 1108 may be the same as or similar to the outer tube 402 of FIG. 4. In other embodiments, however, the body 1108 may comprise an independent structure from the outer tube 402. Various component parts and mechanisms of the end effector 1102 are positioned within the inside or interior of the body 1108. The jaw members 1104, 1106 extend out of or otherwise protrude from the distal end 1110b of the body 1108. In at least one embodiment, the proximal end 1110a may be operatively coupled to an elongate shaft of a surgical tool, such as the shaft 202 of the surgical tool 200 of FIG. 2. In other embodiments, however, the proximal end 1110a may be operatively coupled to an articulable wrist joint, such as the wrist 606 of the surgical tool 600 of FIG. 6.

In some embodiments, the end effector 1102 stores and otherwise houses a plurality of surgical clips 1112. In the illustrated embodiment, the surgical clips are shown arranged in a clip track 1114 positioned within the interior of the body 1108. In other embodiments, however, the body 1108 may define or otherwise provide the clip track 1114. In yet other embodiments, the clip track 1114 may be omitted from the end effector 1102 and the surgical clips 1112 may alternatively be stored proximal to an articulable wrist joint, such as the wrist 606 of the surgical tool 600 of FIG. 6. In such embodiments, the surgical clips 1112 may be required to pass through the articulable wrist joint.

Conventional surgical clips used in clip appliers are commonly pre-formed to a "tissue-ready" state prior to being loaded into an end effector. Tissue-ready surgical clips include a crown (alternately referred to as an "apex") and a pair of legs extending longitudinally from the crown. The legs of the tissue-ready surgical clips are typically received by the jaw members 1104, 1106 in preparation for crimping (crushing) the surgical clip therebetween. Conventional surgical clip appliers store tissue-ready surgical clips in series, where the legs of the more proximal surgical clips engage the crown region of the more distal surgical clips in an axial serial alignment. This storage arrangement maximizes the axial space required to accommodate the surgical clips and thereby reduces the number of clips that can be stored for use.

In contrast, in the illustrated embodiment, the surgical clips 1112 of the present disclosure are stored in the clip track 1114 in an "unformed" state. As used herein, the term "unformed" refers to a surgical clip that is substantially straight and thus not formed (bent) to the tissue-ready state or otherwise able to be properly received between the jaw members 1104, 1106 for crimping. Accordingly, unformed surgical clips are essentially straight or substantially straight lengths of wire, rod, or another elongate material, and are not prepared to ligate anything until it is transformed (bent) into the tissue-ready state. In the unformed state, the surgical clip may not even be referred to as a "surgical clip," per se, but only as a straight wire or rod that may be pre-cut to a predetermined length and is used as the base material to form a surgical clip. In the illustrated embodiment, the surgical clips 1112 are depicted as a plurality of straight rods (or wire) and can be made of a flexible metal, such as titanium.

During the formation process, a surgical clip can pass through several different "states." In general, a surgical clip passes through three states during the formation process: a first state (i.e., the "unformed" state), where the surgical clip comprises a short, substantially straight length of wire (or a rod); a second or "intermediate" state, where the surgical clip has at least one bend along its length; and a third state (i.e., the "tissue-ready" state), where the surgical clip has opposing legs extending from a crown and is ready to be fed into the jaws for crimping. Some users might refer to the surgical clip in the third state as being in the "unformed state," meaning that it has not yet been crimped. However, as used herein, the "unformed" state refers to the surgical clip prior to being bent. In at least one interpretation, the surgical clip also passes through a fourth and final state, where the surgical clip is finally crimped between the opposed jaw members 1104, 1106.

Fully formed or "tissue-ready" surgical clips are traditionally formed into a few known shapes; i.e., U-shaped, V-shaped, box-shaped, W-shaped, paperclip-shaped, etc. Each of these shapes provides two opposed legs or surfaces. In contrast, surgical clips in the "unformed" state do not have opposed legs or surfaces. The present disclosure describes devices, mechanisms, systems, and processes that mechanically manipulate (bend) unformed surgical clips into tissue-ready, surgically usable clips.

Storing the surgical clips 1112 in the unformed state may prove advantageous in being able to accommodate a higher number of surgical clips 1112 within the end effector 1102, which provides a user with a greater number of surgical clips 1112 for use as compared to conventional surgical clips of the same dimension. In the illustrated embodiment, for example, the unformed surgical clips 1112 are stored (stacked) laterally within the clip track 1114, thus accommodating several surgical clips 1112 within the axial length of a single unformed surgical clip 1112. In other embodiments, however, the clip track 1114 may be omitted. In yet other embodiments, the surgical clips 1112 may alternatively be stored proximal to an articulable wrist joint (e.g., the wrist 606 of the surgical tool 600 of FIG. 6) operatively coupled to the end effector 1102. In such embodiments, the unformed surgical clips 1112 may be stored (stacked) either laterally or axially along the length of a shaft (e.g., the elongate shaft 202, 602 of FIGS. 2 and 6, respectively). The unformed surgical clips 1112 may then be advanced longitudinally through the articulable wrist joint to be formed in the end effector 1102, as described below.

To transition the unformed surgical clips 1112 to the tissue-ready state, the end effector 1102 includes a clip forming system 1116 configured to receive unformed surgical clips 1112, plastically deform or bend the unformed surgical clips 1112, and output tissue-ready surgical clips 1112 for receipt by the jaw members 1104, 1106. To accomplish this, the clip forming system 1116 (hereafter "the system 1116") may include a clip receiver feature 1118a, an apex stop feature 1118b, and a bending feature 1118c. The clip receiver feature 1118a may be arranged and otherwise positioned to receive a single (individual) unformed surgical clip, referred to here as a distal-most surgical clip 1112a. Use of the term "distal" in "distal-most surgical clip 1112a" does not require that the distal-most surgical clip 1112a is stacked or stored in a position more distal than the remaining unformed surgical clips 1112, but such could nonetheless be the case. Rather, the term "distal" refers to the distal position of the distal-most surgical clip 1112a relative to the remaining surgical clips 1112 as it is being manipulated to the tissue-ready state by the system 1116, which is located distal to the remaining surgical clips 1112.

The clip receiver feature 1118a may be configured to receive a distal end 1120a of the distal-most surgical clip 1112a as it advances distally. In the illustrated embodiment, the clip receiver feature 1118a comprise a post or pin, but as discussed below variations of the clip receiver feature 1118a may include any structure or receptacle designed to initially receive the distal-most surgical clip 1112a as it advances distally.

The distal-most surgical clip 1112a may be advanced distally toward the system 1116 using any known means, such as a push rod, a feedbar, etc. Once the distal-most surgical clip 1112a advances from the stacked surgical clips 1112, a biasing device 1122 or the like may operate to collapse the remaining surgical clips 1112 and thereby prepare a penultimate surgical clip 1112b to be advanced distally in the next firing sequence. The biasing device 1122 may comprise, for example, a compression spring arrangement or the like that exhibits a constant biasing force on the stacked surgical clips 1112. The biasing device 1122, however, may comprise any other type of biasing mechanism (e.g., a selective or actuatable biasing mechanism) that might help prepare the penultimate surgical clip 1112b for distal movement. As will be appreciated, the arrangement and design of the biasing device 1122 is provided merely for illustrative purposes and may alternatively take on other forms or designs, without departing from the scope of the disclosure.

In some embodiments, the distal-most surgical clip 1112a (and any of the surgical clips 1112) may have one or more retention features 1124 formed thereon or coupled thereto. The retention features 1124 may be configured to engage or come into close contact with the clip receiver feature 1118a and the bending feature 1118c and thereby help maintain the distal-most surgical clip 1112a in a known position during the bending (forming) process. In at least one embodiment, the distal-most surgical clip 1112a (and any of the surgical clips 1112) may further include a detent 1126 configured to engage the apex stop feature 1118b. The detent 1126 may prove advantageous in helping properly form the crown of the distal-most surgical clip 1112a during bending, but may also prove useful in helping maintain the distal-most surgical clip 1112a in a known position while the system 1116 actuates.

In the illustrated embodiment, the system 1116 includes a forming plate 1128 arranged within or otherwise forming part of the body 1108. The clip receiver feature 1118a may be coupled to or extend from the forming plate 1128 and may be generally stationary during operation. In contrast, the apex stop feature 1118b and bending feature 1118c may be actuatable and otherwise movable relative to the body 1108 and the clip receiver feature 1118a. More specifically, the apex stop feature 1118b may be translatable within a first arcuate slot 1130a defined in the forming plate 1128 and the bending feature 1118c may be translatable within a second arcuate slot 1130b defined in the forming plate 1128.

Figure 11B:
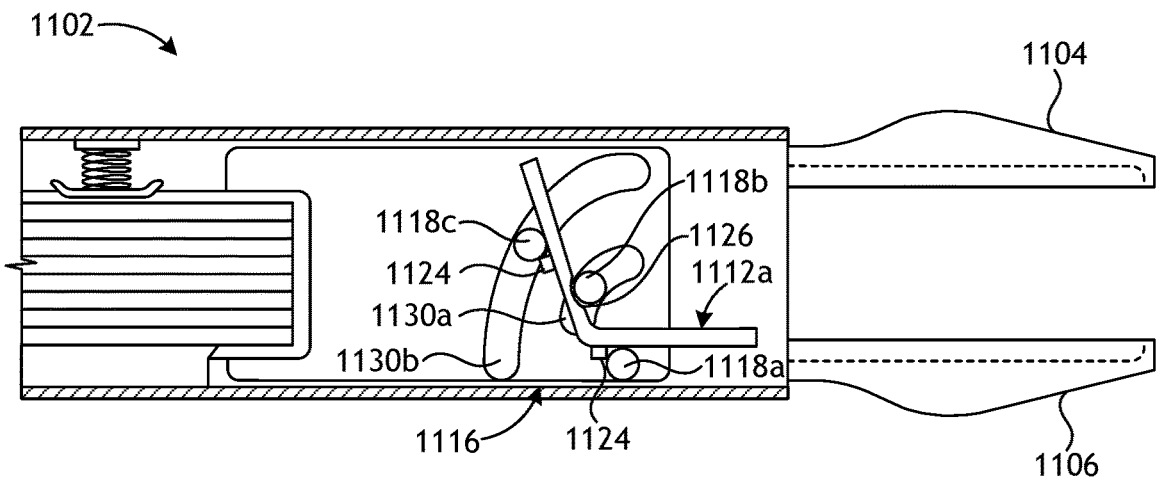
Figure 11C:
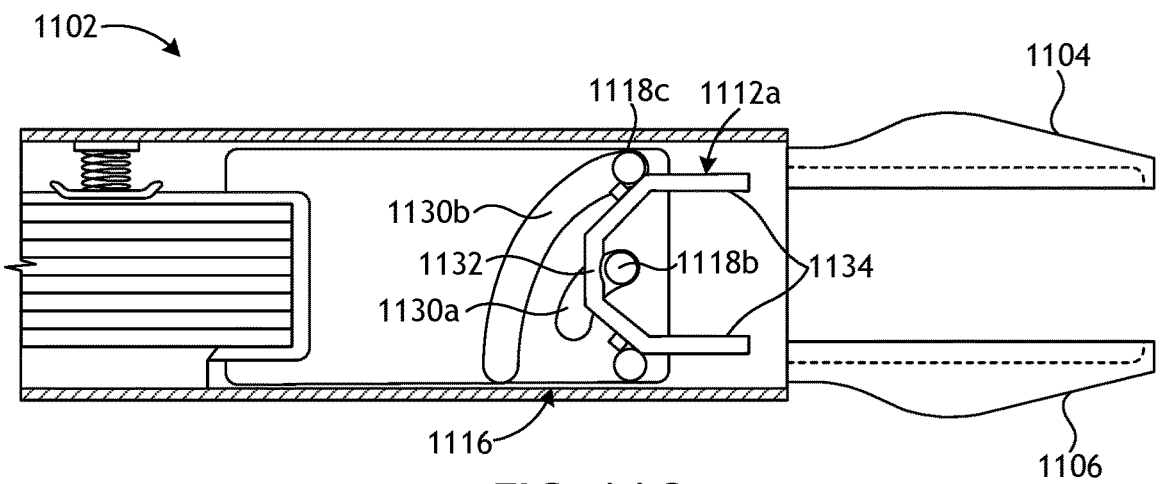
Figure 11D:
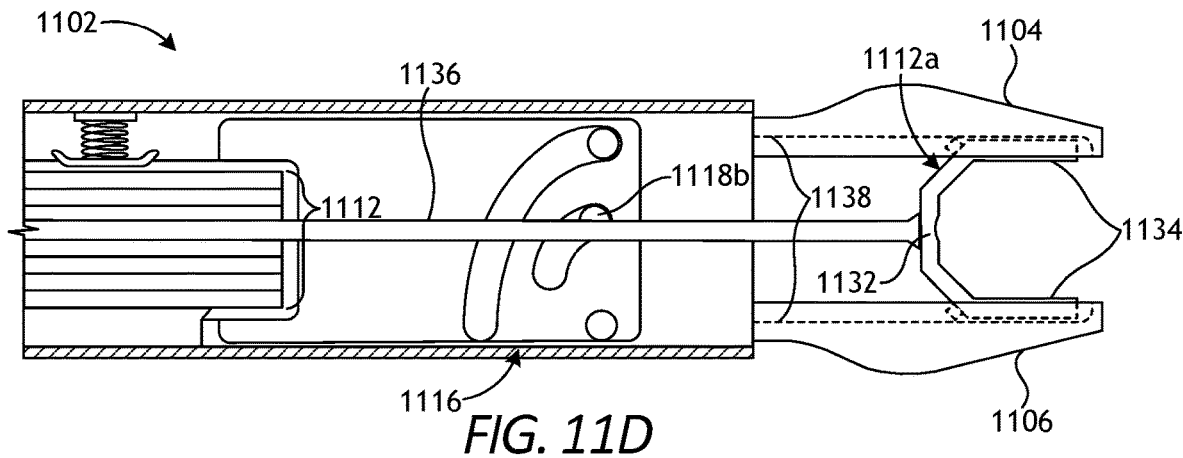

With additional reference to FIGS. 11B-11D, example operation of forming the distal-most surgical clip 1112a to the tissue-ready state and feeding the distal-most surgical clip 1112a into the jaw members 1104, 1106 is now provided. In FIG. 11A, the distal-most surgical clip 1112a is shown advanced distally and received by the system 1116 in the unformed state. In some embodiments, the distal-most surgical clip 1112a is advanced distally a predetermined and known distance using a pusher rod or feedbar extending from a drive housing (e.g., the drive housings 206, 606 of FIGS. 2 and 6, respectively) programmed with software that operates the pusher rod or feedbar. In other embodiments, the pusher rod or feedbar may advance the distal-most surgical clip 1112a distally until the detent 1126 (if included) generally aligns laterally with the apex stop feature 1118b and the retention features 1124 engage or come into close engagement with the clip receiver feature 1118*a* and the bending feature 1118*c*.

Once the distal-most surgical clip 1112*a* is separated (advanced) from the remaining stacked surgical clips 1112, the biasing device 1122 may act on the remaining stacked surgical clips 1112 and position the penultimate surgical clip 1112*b* in queue to be advanced distally during the next firing sequence. Once the distal-most surgical clip 1112*a* is properly positioned, the system 1116 may be actuated to bend (form) the distal-most surgical clip 1112*a* to its tissue-ready state.

In FIG. 11B, the system 1116 is shown being actuated to initially bend the distal-most surgical clip 1112*a*. As will be described in more detail below, actuation of the system 1116 may be realized in a variety of ways. In the illustrated embodiment, actuating the system 1116 causes the apex stop feature 1118*b* and the bending feature 1118*c* to translate within the first and second arcuate slots 1130*a,b*, respectively. Moving the apex and bending features 1118*b,c* urges the distal-most surgical clip 1112*a* laterally against the clip receiver feature 1118*a* and commences formation of the distal-most surgical clip 1112*a* to the tissue-ready state. One or both of the retention features 1124 and the detent 1126 may help maintain the distal-most surgical clip 1112*a* engaged with the clip receiver feature 1118*a* and the posts 1118*b,c* during the bending (forming) process.

In FIG. 11C, the system 1116 has fully actuated to fully bend (form) the distal-most surgical clip 1112*a* into the tissue-ready state. More particularly, the apex stop feature 1118*b* and the bending feature 1118*c* have fully translated (bottomed-out) within the first and second arcuate slots 1130*a,b*, respectively, which results in the distal-most surgical clip 1112*a* defining a crown 1132 and two legs 1134 that extend longitudinally from the crown 1132. In some embodiments, fully actuating the system 1116 may result in the legs 1134 becoming aligned or substantially aligned with the jaw members 1104, 1106.

In FIG. 11D, the distal-most surgical clip 1112*a* is advanced distally from the system 1116 and received within the jaw members 1104, 1106. In at least one embodiment, this may be accomplished using a feedbar 1136. In some embodiments, the feedbar 1136 may engage the distal-most surgical clip 1112*a* at or near the crown 1132, but could alternatively engage the distal-most surgical clip 1112*a* at any other location. In some embodiments, the feedbar 1136 may extend to the end effector 1102 from a drive housing (e.g., the drive housings 206, 606 of FIGS. 2 and 6, respectively). At the drive housing, the feedbar 1136 may be operatively coupled to an actuating mechanism or device configured to cause longitudinal translation of the feedbar 1136. In one embodiment, for example, the feedbar 1136 may be operatively coupled to and otherwise extend from one or more translatable driven gears, such as the second and third driven gears 504*b,c* of FIG. 5. In embodiments with an articulable wrist, the feedbar 1136 may be made of a flexible material and extend through the wrist. Alternatively, the feedbar 1136 may be operatively coupled to a cable-driven gearing arrangement positioned distal to the wrist and the associated drive cable(s) that moves the gear(s) extend(s) through the wrist.

In some embodiments, some or all of the system 1116 may be moved so as to not obstruct distal advancement of the distal-most surgical clip 1112*a* from the system 1116. For instance, at least the apex stop feature 1118*b* may be actuated or otherwise disengaged from the distal-most surgical clip 1112*a* to allow the feedbar 1136 to advance the distal-most surgical clip 1112*a* toward the jaw members 1104, 1106. Means for disengaging the apex stop feature 1118*b* from the distal-most surgical clip 1112*a* are described in more detail below.

In at least one embodiment, each jaw member 1104, 1106 includes a channel or groove 1138 formed on opposed inner surfaces thereof for receiving the distal-most surgical clip 1112*a*. In such embodiments, the grooves 1138 may prove advantageous in helping to capture and maintain the distal-most surgical clip 1112*a* in a known and secure position between the jaw members 1104, 1106. In other embodiments, however, the grooves 1138 may be omitted and the distal-most surgical clip 1112*a* may instead be captured or held between the jaw members 1104, 1106 via an interference fit or the like.

At this point, the jaw members 1104, 1106 may be actuated to collapse or close and thereby crimp the distal-most surgical clip 1112*a* therebetween. As used herein, "actuating" the jaw members 1104, 1106 refers to the mechanical process of collapsing or closing the jaw members 1104, 1106. This can be accomplished via a variety of known means or processes beyond the scope of the present disclosure. Once the distal-most surgical clip 1112*a* is crimped, the foregoing process can be repeated until the supply of remaining surgical clips 1112 is exhausted.

Figure 12A:
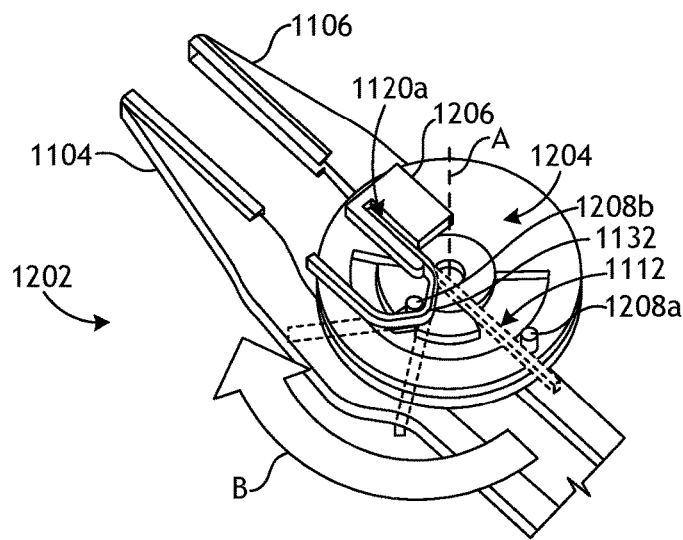
FIG. 12A is an exposed isometric view of another example end effector.

FIG. 12A is an exposed isometric view of another example end effector 1202, according to one or more additional embodiments of the present disclosure. The end effector 1202 may be similar in some respects to the end effector 1102 of FIGS. 11A-11D and therefore may be best understood with reference thereto, where like numerals correspond to similar components not described again in detail. Similar to the end effector 1102, the end effector 1202 may be incorporated into either or both of the surgical tools 200, 600 (FIGS. 2 and 6, respectively), and may comprise a clip applier having the opposed jaw members 1104 and 1106 actuatable to crimp a surgical clip therebetween. Moreover, the end effector 1202 may be configured to transition surgical clips from the unformed state to the tissue-ready state and feed the tissue-ready surgical clips into the jaw members 1104, 1106.

As illustrated, the end effector 1202 includes a clip forming system 1204 configured to receive an unformed surgical clip 1112, plastically deform (bend) the unformed surgical clip 1112, and output a tissue-ready surgical clip 1112 for receipt by the jaw members 1104, 1106. The clip forming system 1204 (hereafter "the system 1204") may include a clip receiver feature 1206, a bending feature 1208*a*, and an apex stop feature 1208*b*. The clip receiver feature 1206 may be arranged and otherwise positioned to initially receive the distal end 1120*a* of the unformed surgical clip 1112 as it advances distally to the system 1204 from a source (not shown) of unformed surgical clips either housed within the end effector 1202 or proximal to the end effector 1202, such as proximal to an articulable wrist operatively coupled to the end effector 1202.

Once the unformed surgical clip 1112 is received by the clip receiver feature 1206, the system 1204 may be actuated to transition the surgical clip 1112 to its tissue-ready state. Actuating the system 1204 results in the bending feature 1208*a* rotating around a central axis A in an angular direction B (clockwise or counter-clockwise) and relative to the clip receiver feature 1206. As discussed below, movement of the apex stop feature 1208*b* in the present embodiment may be caused by rotational movement of the bending feature 1208*a*. As the bending feature 1208*a* rotates about the central axis A, the surgical clip 1112 is correspondingly bent as the apex stop feature 1208b helps forms the crown 1132 and the clip receiver feature 1206 and the bending feature 1208a help form the outer edges or legs 1134.

Figure 12B:
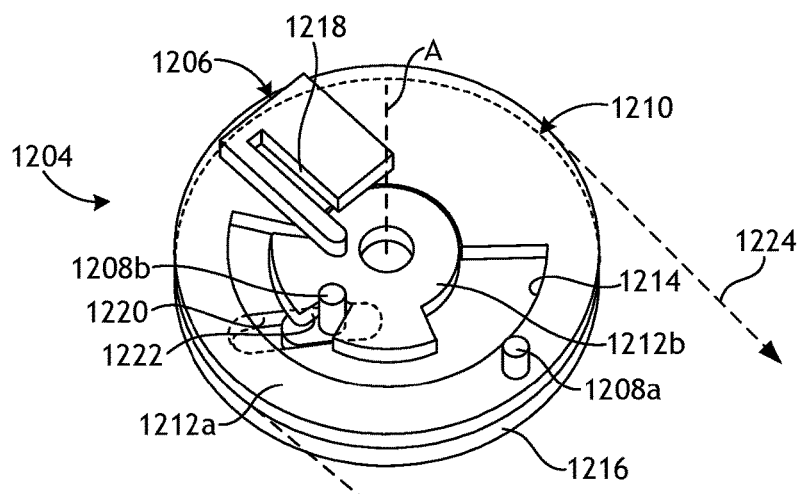
FIG. 12B is an isometric view of the clip forming system of FIG. 12A.

FIG. 12B is an isometric view of the system 1204 of FIG. 12A. The system 1204 includes a forming plate 1210 and the central axis A extends through the center of the forming plate 1210. As illustrated, the forming plate 1210 includes an outer ring 1212a and an inner ring 1212b received within an arcuate slot 1214 at least partially defined by the outer ring 1212a. The system 1204 may further include a substrate 1216 slidably engageable with and otherwise positioned on the underside (bottom) of the forming plate 1210. The substrate 1216 may be generally stationary during operation as the forming plate 1210 rotates about the central axis A.

The clip receiver feature 1206 may be arranged atop the forming plate 1210 and may also be generally stationary during operation. In some embodiments, the substrate 1216 and the clip receiver feature 1206 may be fixed to a stationary internal structure of the end effector 1202 (FIG. 12A), such as a body of the end effector 1202 (e.g., the body 1108 of FIG. 11A), or the outer support tube or shroud of the entire device. The clip receiver feature 1206 could be laser welded, glued, keyed (e.g., similar to a puzzle piece), or otherwise mechanically, thermally, or chemically bonded to the interior surface(s) of the outer support tube. The remaining component parts of the system 1204 may be arranged below that (e.g., closer to the equator of the upper hemisphere). In such embodiments, all clip track or wire-feeding paths might be arranged in the upper-most portion of this hemisphere. The substrate 1216 may be bonded to the same interior surface(s) of the outer support tube. However, the substrate 1206 may be biased below the equator of this hemisphere.

Fixing the substrate 1216 and the clip receiver feature 1206 a stationary internal structure enables the outer ring 1212a to rotate relative to the substrate 1216 and the clip receiver feature 1206. In the illustrated embodiment, the clip receiver feature 1206 defines a slot 1218 configured to receive the distal end 1120a (FIG. 12A) of the surgical clip 1112 (FIG. 12A) as it advances distally to the system 1204.

The bending feature 1208a extends from or is otherwise coupled to the outer ring 1212a such that rotational movement of the outer ring 1212a correspondingly moves the bending feature 1208a in the same angular direction. As illustrated, the apex stop feature 1208b may be positioned within a translation slot 1220 defined in the substrate 1216. The apex stop feature 1208b extends from the translation slot 1220 through a post slot 1222 defined in the inner ring 1212b such that movement of the inner ring 1212b correspondingly moves the apex stop feature 1208b within the translation slot 1220.

The outer ring 1212a may be operatively coupled to a drive input originating at a drive housing (e.g., the drive housings 206, 606 of FIGS. 2 and 6, respectively). In at least one embodiment, for example, the outer ring 1212a may comprise a pulley that may be rotated using one or more drive cables 1224 wrapped at least partially around the outer ring 1212a and extending to one or more capstan pulleys, such as any of the rotatable capstans 1002a-f of FIG. 10. The drive cables 1224 may be similar to the drive cables 808 of FIG. 8, for example. In other embodiments, however, the outer ring 1212a may be rotated by a driven geared arrangement or a combination of a driven gear and cable actuator, without departing from the scope of the disclosure.

FIGS. 13A-13E are progressive top views of the system 1204 showing example operation in bending the surgical clip 1112 into its tissue-ready state. In FIG. 13A, the unformed surgical clip 1112 is shown advanced distally until the distal end 1120a is received within the slot 1218 defined by the clip receiver feature 1206. Once the distal end 1120a is received by the clip receiver feature 1206, the system 1204 can be actuated to commence the clip bending process.

In FIG. 13B, the system 1204 is actuated and thereby rotates the outer ring 1212a in the angular direction B relative to the substrate 1216 and the clip receiver feature 1206. As the outer ring 1212a rotates, the bending feature 1208a engages and starts to bend the surgical clip 1112. More specifically, the surgical clip 1112 may first be bent at the clip receiver feature 1206 where the surgical clip 1112 exits the slot 1218 and thereby forms a first shoulder 1302a. During this rotational movement, the inner ring 1212b remains stationary within the arcuate slot 1214 defined by the outer ring 1212a. Consequently, the apex stop feature 1208b also remains stationary as positioned within the post slot 1222 defined by the inner ring 1212b.

In FIG. 13C, the outer ring 1212a has rotated further in the angular direction B and the bending feature 1208a brings the surgical clip 1112 into contact with the apex stop feature 1208b. Engaging against the apex stop feature 1208b bends the surgical clip 1112 and thereby starts to form the crown 1132. Further rotational movement of the outer ring 1212a will bring an outer wall 1304a defined by the inner ring 1212b into engagement with an opposing inner wall 1304b defined by the outer ring 1212a within the arcuate slot 1214. Once the inner and outer walls 1304a,b come into contact, further rotational movement of the outer ring 1212a will correspondingly move the inner ring 1212b in the same angular direction. Accordingly, the inner ring 1212b may generally operate as a hysteresis ring since its movement lags behind rotational movement of the outer ring 1212a and otherwise until positively engaged by the outer ring 1212a at the opposing inner and outer walls 1304a,b.

Once the outer ring 1212a engages and starts to rotate the inner ring 1212b, the apex stop feature 1208b may be configured to slidably move within the translation slot 1220 defined by the substrate 1216 and thereby exit the post slot 1222 defined by the inner ring 1212b. Moving within the translation slot 1220 allows the apex stop feature 1208b to simultaneously slidably engage the surgical clip 1112 and move away from the location of the crown 1132.

In FIG. 13D, the outer ring 1212a has rotated further in the angular direction B and the apex stop feature 1208b is shown having exited the post slot 1222 as the inner ring 1212b correspondingly rotates in the same direction. In some embodiments, the apex stop feature 1208b may bottom out in the translation slot 1220 at a point where the apex stop feature 1208b is positioned to help bend (form) a second shoulder 1302b of the surgical clip 1112.

Accordingly, the apex stop feature 1208b may be movable to help form (bend) both the crown 1132 and the second shoulder 1302b of the surgical clip 1112. Forming the first and second shoulders 1302a,b helps define and otherwise provide the legs 1134 for the surgical clip 1112 in the tissue-ready state.

In FIG. 13E, the outer ring 1212a may be rotated even further in the angular direction B and the bending feature 1208a may use the apex stop feature 1208b as a fulcrum point to provide an over-bend to the surgical clip 1112 in the tissue-ready state. As known to those skilled in the art, the over-bend may allow for spring-back in the surgical clip 1112, which may be useful in properly seating the surgical clip 1112 between the opposing jaw members 1104, 1106 (FIG. 12A).

At this point, the surgical clip 1112 may be advanced distally into the jaw members 1104, 1106 (FIG. 12A) for crimping, as generally described above. In some embodiments, some or all of the system 1204 may be moved so as to not obstruct distal advancement of the surgical clip 1112 from the system 1204. For instance, at least the apex stop feature 1208b and the clip receiver feature 1206 may be actuated or otherwise disengaged from the surgical clip 1112 to allow a feedbar (e.g., the feedbar 1136 of FIG. 11D) to advance the surgical clip 1112 toward the jaw members 1104, 1106.

FIG. 14A is an exposed isometric view of another example end effector 1402, according to one or more additional embodiments of the present disclosure. The end effector 1402 may be similar in some respects to the other end effectors described in this disclosure, and thus may be incorporated into either or both of the surgical tools 200, 600 (FIGS. 2 and 6, respectively). Moreover, the end effector 1402 may comprise a clip applier having the opposed jaw members 1104 and 1106 actuatable to crimp a surgical clip therebetween. In addition, the end effector 1402 may be configured to form (bend) unformed surgical clips to a tissue-ready state and feed the tissue-ready surgical clips into the jaw members 1104, 1106 for crimping.

As illustrated, the end effector 1402 includes a clip forming system 1404 configured to receive an unformed surgical clip 1112, plastically deform (bend) the unformed surgical clip 1112, and output a tissue-ready surgical clip 1112 for receipt by the jaw members 1104, 1106. The clip forming system 1404 (hereafter "the system 1404") is similar in some respects to the system 1204 of FIG. 12A and therefore may be best understood with reference thereto. Similar to the system 1204, for example, the system 1404 may include the clip receiver feature 1206, the bending feature 1208a, and the apex stop feature 1208b.

Once the distal end 1120a of the unformed surgical clip 1112 is received by the clip receiver feature 1206, the system 1404 is actuated to transition the surgical clip 1112 to its tissue-ready state. Actuating the system 1404 rotates the bending feature 1208a around the central axis A in the angular direction B and relative to the clip receiver feature 1206. Moreover, movement of the apex stop feature 1208b may be caused by rotational movement of the bending feature 1208a. As the bending feature 1208a rotates, the surgical clip 1112 is correspondingly bent around the apex stop feature 1208b and the clip receiver feature 1206 to cooperatively form the crown 1132 and the legs 1134.

FIG. 14B is an isometric top view of the system 1404 of FIG. 14A. The system 1404 includes a forming plate 1406 and the central axis A extends through the center of the forming plate 1406. As illustrated, the forming plate 1406 may comprise an upper plate 1407 and a substrate 1408 slidably engageable with and otherwise positioned on the underside (bottom) of the upper plate 1407. The substrate 1408 may be generally stationary during operation as the upper plate 1407 rotates about the central axis A. The clip receiver feature 1206 (FIG. 14A) may be arranged atop the forming plate 1406 (e.g., the upper plate 1407) and may also be generally stationary during operation.

The bending feature 1208a extends from or is otherwise coupled to the upper plate 1407 such that rotational movement of the upper plate 1407 correspondingly moves the bending feature 1208a in the same angular direction. As illustrated, the apex stop feature 1208b may be movably positioned within a translation slot 1410 (shown partially in phantom) defined in the substrate 1408. The apex stop feature 1208b extends through a cam slot 1412 defined in the upper plate 1407 such that movement of the upper plate 1407 correspondingly moves the apex stop feature 1208b within the cam slot 1412. The cam slot 1412 may be defined and otherwise configured to guide the apex stop feature 1208b to specific interval positions that allow the apex stop feature 1208b to help form various bends in the surgical clip 1112 (FIG. 14A). As described below, such movement requires the apex stop feature 1208b to slidably translate within the translation slot 1410, as needed.

The forming plate 1406 (e.g., the upper plate 1407) may be operatively coupled to a drive input originating at a drive housing (e.g., the drive housings 206, 606 of FIGS. 2 and 6, respectively). In at least one embodiment, for example, the upper plate 1407 may comprise a pulley that may be rotated using one or more drive cables 1224 wrapped at least partially around the upper plate 1407 and extending to one or more capstan pulleys, such as any of the rotatable capstans 1002a-f of FIG. 10. In other embodiments, however, the upper plate 1407 may be rotated by a driven geared arrangement or a combination of a driven gear and cable actuator, without departing from the scope of the disclosure.

FIG. 14C is an isometric bottom view of the system 1404. As illustrated, the substrate 1408 is shown positioned on the underside (bottom) of the upper plate 1407. In some embodiments, the system 1404 may further include a torsion spring 1414 operable to help the upper plate 1407 return to a known "home" position following actuation of the system 1404 and resultant formation of a surgical clip to the tissue-ready state. One end of the torsion spring 1414 may be operatively coupled (either directly or indirectly) to the upper plate 1407. In some embodiments, as illustrated, the torsion spring 1414 may be operatively coupled to the upper plate 1407 at a coupling member 1416 located and otherwise fixed to the bottom of the upper plate 1407. The other end of the torsion spring 1414 may be operatively coupled (either directly or indirectly) to the substrate 1408. In the illustrated embodiment, for example, the torsion spring 1414 is wrapped around a central pin 1418 fixed to the substrate 1408. In other embodiments, however, the torsion spring 1414 may be directly coupled to the substrate 1408, without departing from the scope of the disclosure.

In operation, the upper plate 1407 will rotate relative to the substrate 1408 and simultaneously build up spring force in the torsion spring 1414. Once the system 1404 completes its actuation, the built up spring force of the torsion spring 1414 may be released and cause the upper plate 1407 to return to the home position to start the clip forming process over again.

As will be appreciated, a passive, "always on" spring return provided by the torsion spring 1414 may be advantageous over a motor-driven return actuated from the drive housing (e.g., the drive housings 206, 606 of FIGS. 2 and 6, respectively). If the motor fails at the drive housing, for example, or some aspect of the drive train extending to the drive housing fails, the torsion spring 1414 will continue to work and the system will return to home. This may allow for less risk of jammed clips or jaws. A passive spring return also allows for less complexity in the system 1404, as it would only need to pull in one direction to actuate, and does not require reverse direction and push to return to home.

While depicted in FIG. 14C as a type of coil torsion spring, the torsion spring 1414 may alternatively comprise a straight leaf spring. In such embodiments, one end of the torsion spring 1414 may be operatively coupled (either directly or indirectly) to the upper plate 1407, such as at the coupling member 1416, and the other end of the torsion spring may be operatively coupled (either directly or indirectly) to the substrate 1408. As the upper plate 1407 departs from home, the torsion spring 1414 flexes and returns to a natural straight configuration when it is at rest.

FIGS. 15A-15E are progressive top views of the system 1404 showing example operation in bending the surgical clip 1112 into its tissue-ready state. In FIG. 15A, the unformed surgical clip 1112 is shown advanced distally until the distal end 1120a is received within the slot 1218 defined by the clip receiver feature 1206. Once the distal end 1120a is received by the clip receiver feature 1206, the system 1404 can be actuated to commence the clip bending process.

In FIG. 15B, the system 1404 is actuated and the upper plate 1407 starts to rotate in the angular direction B relative to the substrate 1408 and the clip receiver feature 1206. As the upper plate 1407 rotates, the bending feature 1208a engages and starts to bend the surgical clip 1112. More specifically, the surgical clip 1112 may first be bent at the clip receiver feature 1206 where the surgical clip 1112 exits the slot 1218 and thereby forms the first shoulder 1302a. During rotational movement of the upper plate 1407, the apex stop feature 1208b may be configured to slidably follow the profile of the cam slot 1412 but remain substantially stationary within the translation slot 1410 defined in the substrate 1408. In some applications, the apex stop feature 1208b may move a small distance, as determined by the torsion spring 1414 (FIG. 14C), the size of the translation slot 1410, and the size of the surgical clip 1112.

In FIG. 15C, the upper plate 1407 has rotated further in the angular direction B and the bending feature 1208a brings the surgical clip 1112 into contact with the apex stop feature 1208b. Engaging against the apex stop feature 1208b bends the surgical clip 1112 and forms the crown 1132. Further rotational movement of the upper plate 1407 will guide the apex stop feature 1208b through a radially-extending portion 1502 of the profile of the cam slot 1412. Within the radially-extending portion 1502, the apex stop feature 1208b may be able to move radially outward and simultaneously slide within the translation slot 1410 in the same direction. Moving within the translation slot 1410 allows the apex stop feature 1208b to simultaneously slide along the surgical clip 1112 and thereby move away from the location of the crown 1132.

In FIG. 15D, the upper plate 1407 has rotated further in the angular direction B and the apex stop feature 1208b is shown having bottomed out in the translation slot 1410 and/or the radially-extending portion 1502 of the cam slot 1412. In some embodiments, the apex stop feature 1208b bottoms out at a point positioned to help bend (form) the second shoulder 1302b of the surgical clip 1112. Accordingly, the apex stop feature 1208b may be movable within the cam and translation slots 1410, 1412 to help form (bend) both the crown 1132 and the second shoulder 1302b of the surgical clip 1112.

In FIG. 15E, the upper plate 1407 may be rotated even further in the angular direction B and the bending feature 1208a may use the apex stop feature 1208b as a fulcrum point to provide an over-bend to the surgical clip 1112. At this point, the surgical clip 1112 may be advanced distally into the jaw members 1104, 1106 (FIG. 14A) for crimping, as generally described above. In some embodiments, some or all of the system 1404 may be moved so as to not obstruct distal advancement of the surgical clip 1112 from the system 1404. For instance, at least the apex stop feature 1208b and the clip receiver feature 1206 may be actuated or otherwise disengaged from the surgical clip 1112 to allow a feedbar (e.g., the feedbar 1136 of FIG. 11D) to advance the surgical clip 1112 toward the jaw members 1104, 1106.

FIGS. 16A-16E illustrate progressive views of another example end effector 1602 during example operation of forming a surgical clip to the tissue-ready state, according to one or more additional embodiments of the present disclosure. The end effector 1602 may be similar in some respects to the other end effectors introduced herein, and thus may be incorporated into either or both of the surgical tools 200, 600 (FIGS. 2 and 6, respectively). Moreover, the end effector 1602 may comprise a clip applier having the opposed jaw members 1104 and 1106 actuatable to crimp a surgical clip therebetween. In addition, the end effector 1602 may be configured to form (bend) unformed surgical clips and feed tissue-ready surgical clips into the jaw members 1104, 1106 for crimping.

Figure 16A:
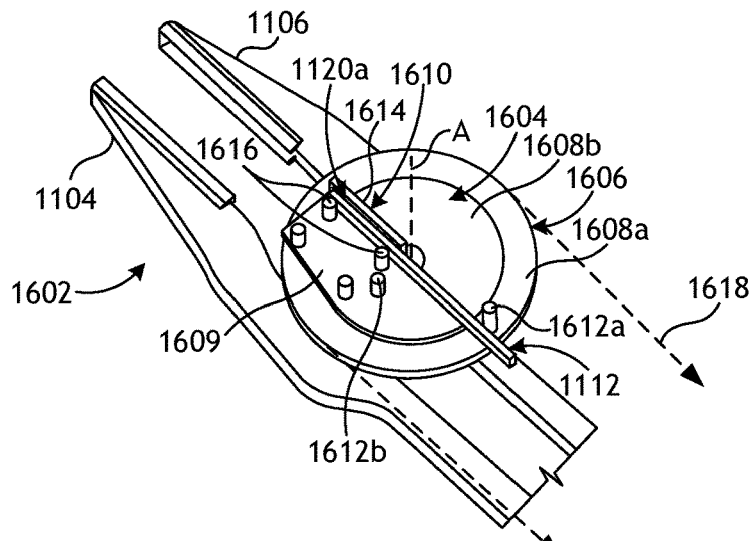
FIGS. 16A-16E illustrate progressive views of another example end effector during example operation of forming a surgical clip to the tissue-ready state.

Referring first to FIG. 16A, the end effector 1602 includes a clip forming system 1604 configured to receive an unformed surgical clip 1112, plastically deform (bend) the unformed surgical clip 1112, and output a tissue-ready surgical clip 1112 for receipt by the jaw members 1104, 1106. The clip forming system 1604 (hereafter "the system 1604") is similar in some respects to the systems 1204 and 1404 of FIGS. 12A and 14A, respectively, and therefore may be best understood with reference thereto.

The system 1604 includes a forming plate 1606 and a central axis A extends through the center of the forming plate 1606. As illustrated, the forming plate 1606 includes an outer ring 1608a and an inner ring 1608b generally positioned within the outer ring 1608a. In some embodiments, the inner ring 1608b may be concentrically positioned within the outer ring 1608a, but such an arrangement is not necessary. During actuation of the system 1604, the outer ring 1608a rotates about the central axis A and relative to the inner ring 1608b, which remains generally stationary.

In at least one embodiment, the system 1604 may further include a clip forming jig 1609 that incorporates or otherwise includes various structural elements or devices used to help bend the surgical clip 1112. The clip forming jig 1609 may be operatively coupled to or otherwise form an integral part of the inner ring 1608b. Consequently, the clip forming jig 1609 may remain stationary with the inner ring 1608b during actuation of the system 1604.

The system 1604 may also include a clip receiver feature 1610, a bending feature 1612a, and an apex stop feature 1612b. The clip receiver feature 1610 may be arranged on the forming plate 1606 and, more particularly, on the clip forming jig 1609 or alternatively the inner ring 1608b. Accordingly, the clip receiver feature 1610 may be generally stationary during actuation of the system 1604. In some embodiments, the clip receiver feature 1610 may comprise an integral extension of the clip forming jig 1609 (or alternatively the inner ring 1608b), but may otherwise comprise an independent structure coupled thereto.

The clip receiver feature 1610 may be arranged and otherwise positioned to initially receive the distal end 1120a of the unformed surgical clip 1112 as it advances distally to the system 1604. In the illustrated embodiment, the clip receiver feature 1610 includes a longitudinally-extending plate 1614 extending longitudinally and at least one leg pin 1616 (two shown) laterally offset from the plate 1614. The plate 1614 and the leg pin(s) 1616 may be configured to receive and accommodate the distal end 1120a of the unformed surgical clip 1112 therebetween. In other embodiments, as will be appreciated, the plate 1614 may be replaced with two or more pins (e.g., the leg pin(s) 1616), and the leg pin(s) 1616 may be replaced with a longitudinally-extending plate (e.g., the plate 1614), without departing from the scope of the disclosure.

The bending feature 1612a extends from or is otherwise coupled to the outer ring 1608a such that rotational movement of the outer ring 1608a correspondingly moves the bending feature 1612a in the same angular direction. In contrast, the apex stop feature 1612b may extend from the clip forming jig 1609 (or alternatively the inner ring 1608b) and thus remains stationary during actuation of the system 1604.

The outer ring 1608a may be rotated through a drive input originating at a drive housing (e.g., the drive housings 206, 606 of FIGS. 2 and 6, respectively). In at least one embodiment, for example, the outer ring 1608a may comprise a pulley that may be rotated using one or more drive cables 1618 wrapped at least partially around the outer ring 1608a and extending to one or more capstan pulleys, such as any of the rotatable capstans 1002a-f of FIG. 10. The drive cables 1618 may be similar to the drive cables 808 of FIG. 8, for example. In other embodiments, however, the outer ring 1608a may be rotated by a driven geared arrangement or a combination of a driven gear and cable actuator, without departing from the scope of the disclosure.

With additional reference to FIGS. 16B-16E, example operation of forming the surgical clip 1112 to its tissue-ready state is now provided. In FIG. 16A, the unformed surgical clip 1112 is shown as having been advanced distally until the distal end 1120a is received by the clip receiver feature 1610 and, more particularly, between the plate 1614 and the leg pin(s) 1616. Once the distal end 1120a is received by the clip receiver feature 1610, the system 1604 can be actuated to commence the clip bending process.

Figure 16B:
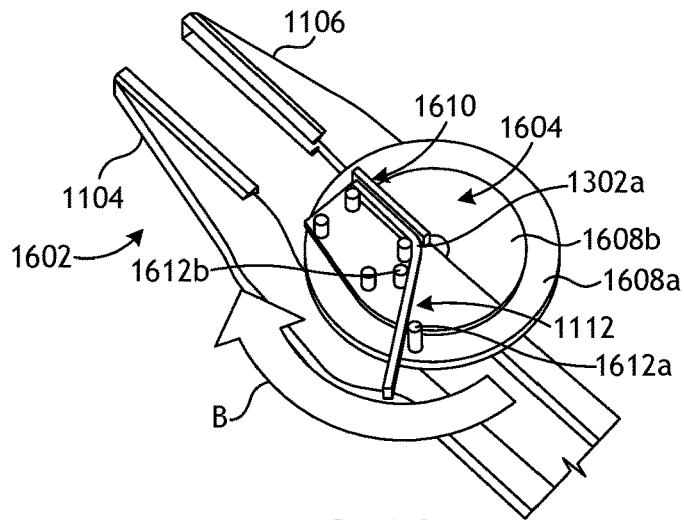

In FIG. 16B, the system 1604 is actuated and thereby rotates the outer ring 1608a in the angular direction B relative to the inner ring 1608b and, thus, relative to the clip receiver feature 1610 and the apex stop feature 1612b. As the outer ring 1608a rotates, the bending feature 1612a engages and starts to bend the surgical clip 1112. More specifically, the surgical clip 1112 may first be bent at the clip receiver feature 1610 and thereby forms the first shoulder 1302a.

Figure 16C:
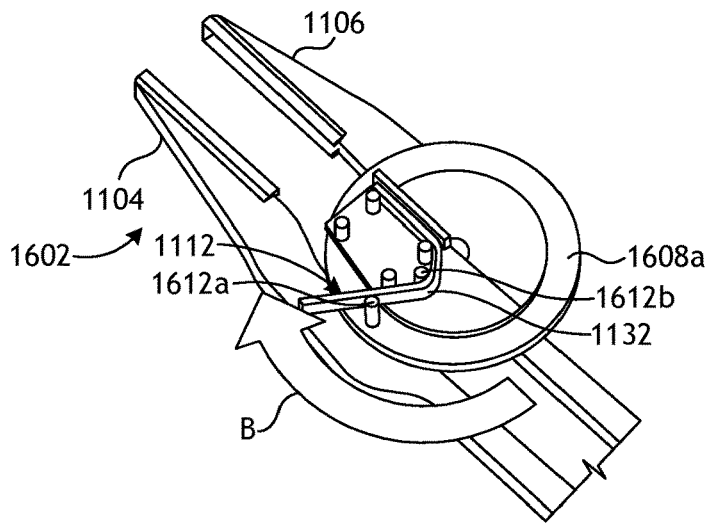

In FIG. 16C, the outer ring 1608a has rotated further in the angular direction B and the bending feature 1612a brings the surgical clip 1112 into contact with the apex stop feature 1612b. Engaging the surgical clip 1112 against the apex stop feature 1612b bends the surgical clip 1112 at that point and starts to form the crown 1132.

Figure 16D:
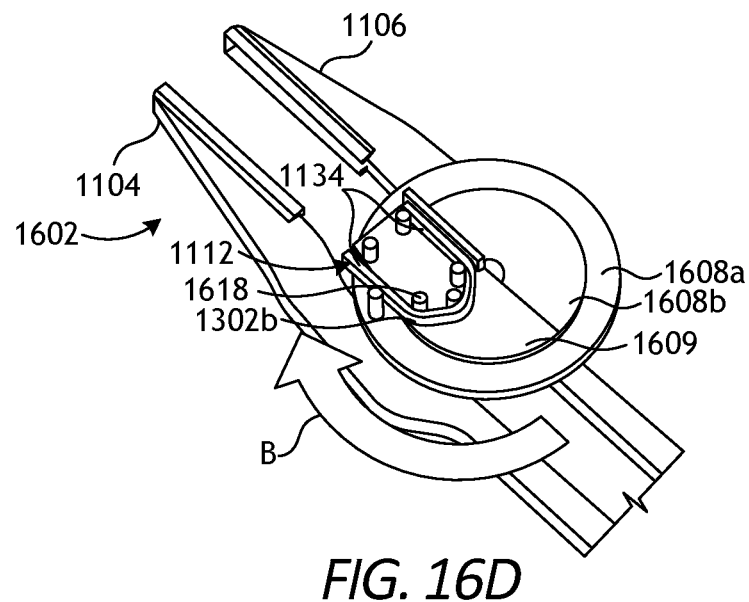

In FIG. 16D, the outer ring 1608a has rotated further in the angular direction B and brought the surgical clip 1112 into engagement with a shoulder post 1618. The shoulder post 1618 may be laterally offset from the apex stop feature 1612b and extend from the clip forming jig 1609 (or alternatively the inner ring 1608b). The shoulder post 1618 may be positioned to help bend (form) the second shoulder 1302b of the surgical clip 1112. Forming the first and second shoulders 1302a,b helps define and otherwise provide the legs 1134 for the surgical clip 1112.

Figure 16E:
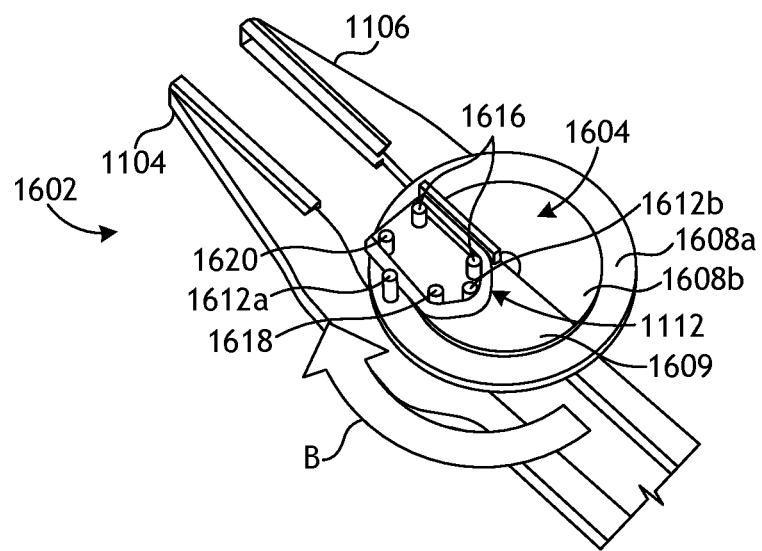

In FIG. 16E, the outer ring 1608a may be rotated even further in the angular direction B and the bending feature 1612a may use the shoulder post 1618 as a fulcrum point to provide an over-bend to the surgical clip 1112. In some embodiments, as illustrated, the system 1604 may further include a supplemental leg pin 1620 positioned to prevent the bending feature 1612a from exceeding a desired over-bend magnitude for the surgical clip 1112. The supplemental leg pin 1620 may extend from the clip forming jig 1609 (or alternatively the inner ring 1608b). In other embodiments, however, the supplemental leg pin 1620 may be omitted and the bending feature 1612a may instead be rotated a known (metered) amount to provide the desired over-bend magnitude, without departing from the scope of the disclosure.

At this point, the surgical clip 1112 may be advanced distally into the jaw members 1104, 1106 for crimping, as generally described above. In some embodiments, some or all of the system 1604 may be moved so as to not obstruct distal advancement of the surgical clip 1112 from the system 1604. For instance, at least the leg pin(s) 1616, the apex stop feature 1612b, the shoulder post 1618, and the supplemental leg pin 1620 may be moved or otherwise disengaged from the surgical clip 1112 to allow a feedbar (e.g., the feedbar 1136 of FIG. 11D) to advance the surgical clip 1112 from the system 1604 and toward the jaw members 1104, 1106.

FIGS. 17A-17E illustrate progressive views of another example end effector 1702 during example operation of forming a surgical clip to the tissue-ready state, according to one or more additional embodiments of the present disclosure. The end effector 1702 may be similar in some respects to the other end effectors described herein and thus may be incorporated into either or both of the surgical tools 200, 600 (FIGS. 2 and 6, respectively). Moreover, the end effector 1702 may comprise a clip applier having the opposed jaw members 1104 and 1106 actuatable to crimp a surgical clip therebetween. In addition, the end effector 1702 may be configured to form (bend) unformed surgical clips and feed tissue-ready surgical clips into the jaw members 1104, 1106 for crimping.

Figure 17A:
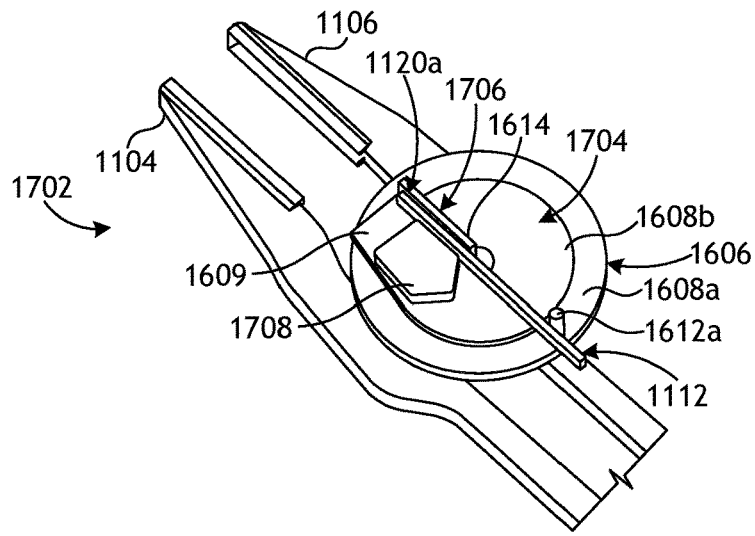
FIGS. 17A-17E illustrate progressive views of another example end effector during example operation of forming a surgical clip to the tissue-ready state.

Referring first to FIG. 17A, the end effector 1702 includes a clip forming system 1704 configured to receive an unformed surgical clip 1112, plastically deform (bend) the unformed surgical clip 1112, and output a tissue-ready surgical clip 1112 for receipt by the jaw members 1104, 1106. The clip forming system 1704 (hereafter "the system 1704") is similar in some respects to the system 1604 of FIGS. 16A-16E, and therefore may be best understood with reference thereto, where like numerals will represent like components or elements not described again. For example, the system 1704 includes the forming plate 1606, including the outer ring 1608a, the inner ring 1608b, and optionally the clip forming jig 1609. The clip forming jig 1609 or alternatively the inner ring 1608b may incorporate or otherwise include various structural elements or devices used to help bend the surgical clip 1112. The system 1704 also includes the bending feature 1612a extending from or otherwise coupled to the outer ring 1608a.

The system 1704 may also include a clip receiver feature 1706 and an apex stop feature 1708. The clip receiver feature 1706 may be arranged on the forming plate 1606 and, more particularly, on the clip forming jig 1609 (or alternatively the inner ring 1608b). Accordingly, the clip receiver feature 1706 may be generally stationary during actuation of the system 1704. In some embodiments, the clip receiver feature 1706 may comprise an integral extension of the clip forming jig 1609 (or alternatively the inner ring 1608b), but may otherwise comprise an independent structure coupled thereto.

The clip receiver feature 1706 may be arranged and otherwise positioned to initially receive the distal end 1120a of the unformed surgical clip 1112 as it advances distally to the system 1704. In the illustrated embodiment, the clip receiver feature 1706 comprises the plate 1614, but the plate 1614 could alternatively be replaced with (or combined with) one or more leg pins 1616 (FIG. 16A), without departing from the scope of the disclosure.

The apex stop feature 1708 may be coupled to or otherwise extend from the clip forming jig 1609 (or alternatively the inner ring 1608b) and thus remains stationary during actuation of the system 1704. As illustrated, the apex stop feature 1708 may comprise a polygonal-shaped structure that provides the basic bend pattern for the tissue-ready surgical clip 1112. In the illustrated embodiment, the apex stop feature 1708 exhibits a pentagonal shape, but might alternatively exhibit other suitable shapes configured to bend the surgical clip 1112. In the illustrated embodiment, one side of the apex stop feature 1708 may cooperatively receive the distal end 1120a of the unformed surgical clip 1112 with the clip receiver feature 1706. In other embodiments, the distal end 1120a of the unformed surgical clip 1112 with may be received between one or more leg pins 1616 (FIG. 16A) and the plate 1614, without departing from the scope of the disclosure.

With additional reference to FIGS. 17B-17E, example operation of forming the surgical clip 1112 to its tissue-ready state is now provided. In FIG. 17A, the unformed surgical clip 1112 is shown as having been advanced distally until the distal end 1120a is received by the clip receiver feature 1706 and, more particularly, between the plate 1614 and a sidewall of the apex stop feature 1708. Once the distal end 1120a is received by the clip receiver feature 1706, the system 1704 can be actuated to commence the clip bending process.

Figure 17B:
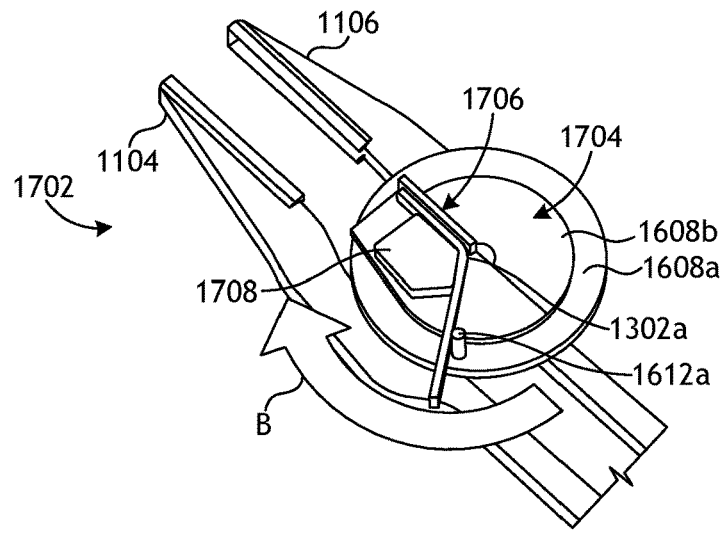

In FIG. 17B, the system 1704 is actuated and thereby rotates the outer ring 1608a in the angular direction B relative to the inner ring 1608b and, thus, relative to the clip receiver feature 1706 and the apex stop feature 1708. As the outer ring 1608a rotates, the bending feature 1612a engages and starts to bend the surgical clip 1112 around the apex stop feature 1708. More specifically, the surgical clip 1112 may first be bent against the apex stop feature 1708 at the clip receiver feature 1706 and thereby forms the first shoulder 1302a.

Figure 17C:
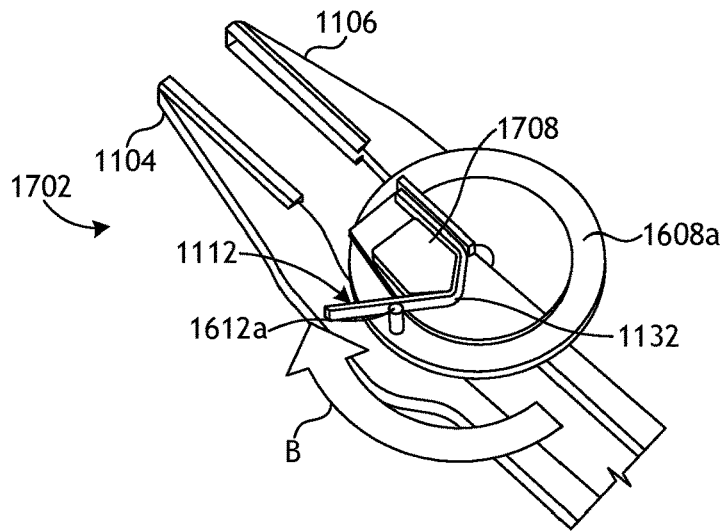

In FIG. 17C, the outer ring 1608a has rotated further in the angular direction B and the bending feature 1612a bends the surgical clip 1112 more around the apex stop feature 1708, and thus forming the crown 1132.

Figure 17D:
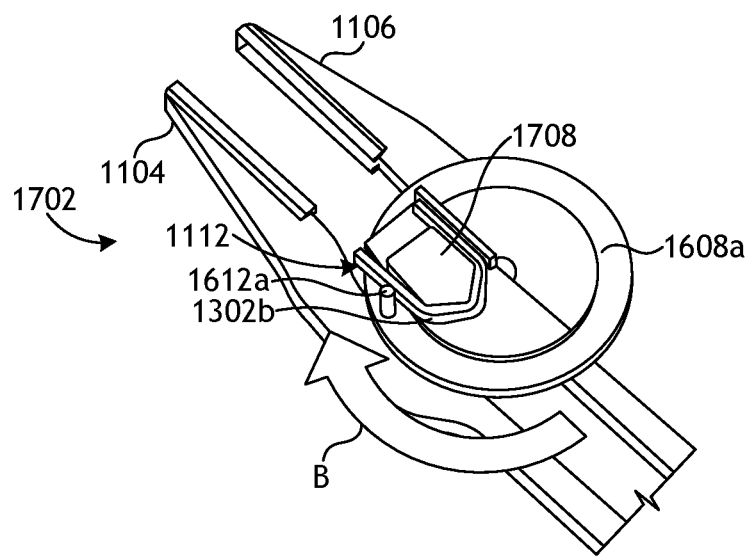

In FIG. 17D, the outer ring 1608a has rotated further in the angular direction B and the bending feature 1612a has essentially bent the surgical clip 1112 around four contiguous sides of the apex stop feature 1708, and thereby formed the second shoulder 1302b of the surgical clip 1112.

Figure 17E:
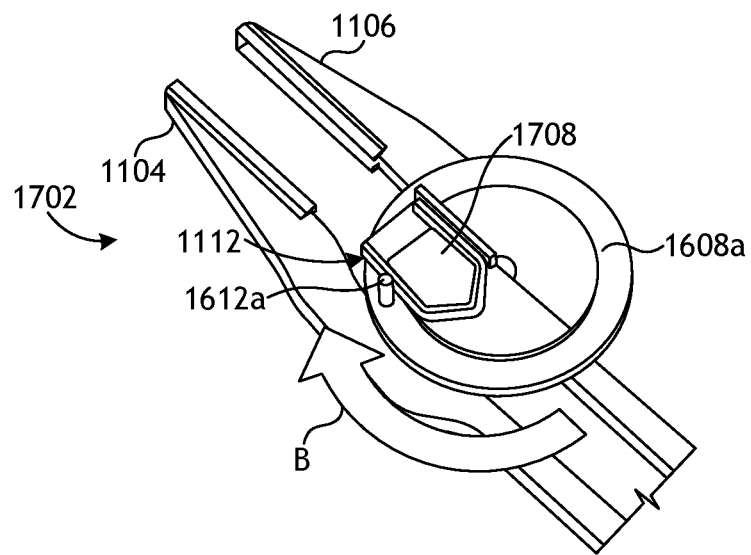

In FIG. 17E, the outer ring 1608a may be rotated even further in the angular direction B and the bending feature 1612a may use a sidewall of the apex stop feature 1708 as a fulcrum point to provide an over-bend to the surgical clip 1112. At this point, the surgical clip 1112 may be advanced distally into the jaw members 1104, 1106 for crimping, as generally described above. In some embodiments, some or all of the system 1704 may be moved so as to not obstruct distal advancement of the surgical clip 1112 from the system 1704. For instance, at least the apex stop feature 1708 may be moved or otherwise disengaged from the surgical clip 1112 to allow a feedbar (e.g., the feedbar 1136 of FIG. 11D) to advance the surgical clip 1112 toward the jaw members 1104, 1106.

Figure 18:
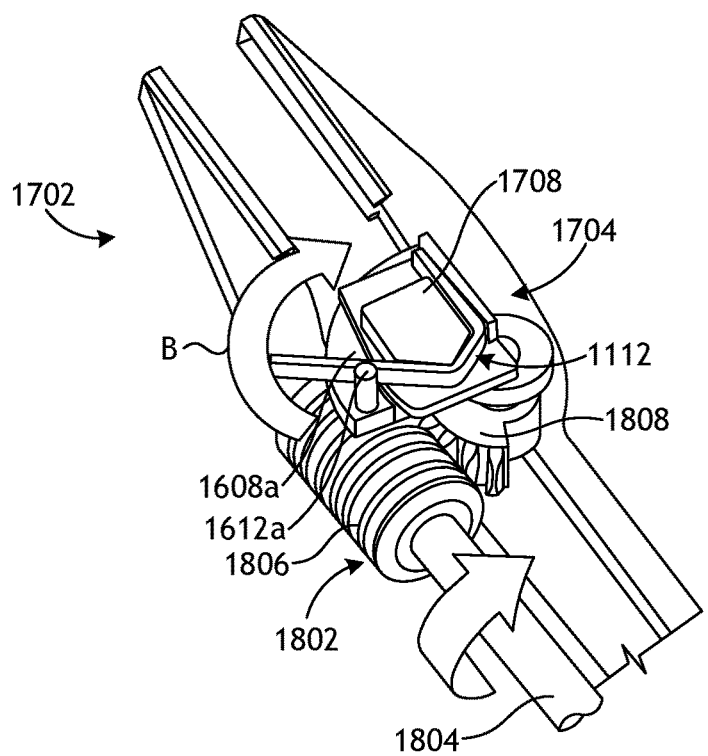
FIG. 18 depicts an example actuation mechanism that may be incorporated into an end effector and used to actuate a clip forming system.

FIG. 18 depicts an example actuation mechanism 1802 that may be incorporated into an end effector and used to actuate a clip forming system to transition unformed surgical clips to tissue-ready surgical clips. More specifically, FIG. 18 shows the actuation mechanism 1802 incorporated into the end effector 1702 of FIGS. 17A-17E and used to actuate the system 1704. It will be appreciated, however, that the actuation mechanism 1802 may alternatively be incorporated into any of the end effectors described herein, without departing from the scope of the disclosure.

As illustrated, the actuation mechanism 1802 may include a drive shaft 1804 and a worm gear 1806 positioned at the distal end of the drive shaft 1804. In some embodiments, the drive shaft 1804 may extend from a drive housing (e.g., the drive housings 206, 606 of FIGS. 2 and 6, respectively), and the drive shaft 1804 may be operatively coupled to an actuating mechanism or device positioned on the drive housing and configured to cause rotation of the drive shaft 1804. In one embodiment, for example, the drive shaft 1804 may be operatively coupled to and otherwise extend from a helical gear arrangement, similar to the first drive and driven gears 502a, 504a of FIG. 5. In embodiments with an articulable wrist, the drive shaft 1804 may be made of a flexible material and capable of extending through the wrist. In other embodiments, however, the drive shaft 1804 may not extend to a drive housing but may instead be operatively coupled to a cable-driven gearing arrangement positioned distal to an articulable wrist and the associated drive cable(s) that moves the gear(s) extend(s) through the wrist.

Rotation of the drive shaft 1804 correspondingly rotates the worm gear 1806, which intermeshes with a driven gear 1808. The driven gear 1808 may be operatively coupled (either directly or indirectly) to the outer ring 1608a such that rotation of the driven gear 1808 correspondingly rotates the outer ring 1608a and the bending feature 1612a in the angular direction B. Consequently, rotating the drive shaft 1804 correspondingly rotates the outer ring 1608a in the angular direction B and thereby causes the bending feature 1612a to progressively bend the surgical clip 1112 around the apex stop feature 1708 to the tissue-ready state. This directly geared drive may provide substantially higher forming forces and near-zero backlash, as compared to a cable and capstan driven option. However, both options would work with any of the clip forming systems described herein.

Figure 19:
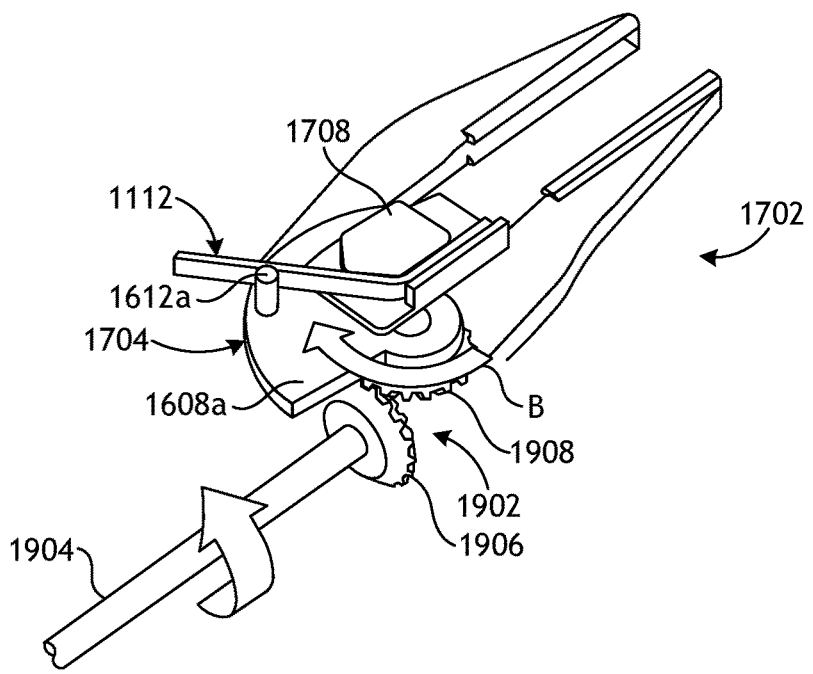
FIG. 19 depicts another example actuation mechanism that may be incorporated into an end effector and used to actuate a clip forming system.

FIG. 19 depicts another example actuation mechanism 1902 used to actuate a clip forming system to transition unformed surgical clips to tissue-ready surgical clips. FIG. 19 shows the actuation mechanism 1902 incorporated into the end effector 1702 of FIGS. 17A-17E and used to actuate the system 1704. Again, however, it will be appreciated that the actuation mechanism 1902 may alternatively be incorporated into any of the end effectors described herein, without departing from the scope of the disclosure.

As illustrated, the actuation mechanism 1902 may include a drive shaft 1904 and a bevel gear 1906 positioned at the distal end of the drive shaft 1904. Similar to the drive shaft 1804 of FIG. 18, the drive shaft 1904 may extend from a drive housing (e.g., the drive housings 206, 606 of FIGS. 2 and 6, respectively) where the drive shaft 1904 may be operatively coupled to an actuating mechanism or device configured to cause rotation of the drive shaft 1904. In other embodiments, however, the drive shaft 1904 may not extend to a drive housing but may instead be operatively coupled to a cable-driven gearing arrangement positioned distal to an articulable wrist and the associated drive cable(s) that moves the gear(s) extend(s) through the wrist.

Rotation of the drive shaft 1904 correspondingly rotates the bevel gear 1906, which intermeshes with a corresponding driven gear 1908. The driven gear 1908 may be operatively coupled (either directly or indirectly) to the outer ring 1608a such that rotation of the driven gear 1908 correspondingly rotates the outer ring 1608a and the bending feature 1612a in the angular direction B. Consequently, rotating the drive shaft 1904 correspondingly rotates the outer ring 1608a in the angular direction B and thereby causes the bending feature 1612a to progressively bend the surgical clip 1112 around the apex stop feature 1708 to the tissue-ready state.

In some embodiments, one or both of the bevel gears 1906, 1908 may not encompass an entire circle (i.e. they may be gear-teeth formed onto a semicircle, quarter-circle, or any other arc) in order to be housed within the tight space constraints of the device shaft. Moreover, as with the embodiment of FIG. 18, this directly geared drive may also provide substantially higher forming forces and near-zero backlash, as compared to a cable and capstan driven option. However, both options would work with any of the clip forming systems described herein.

Figure 20:
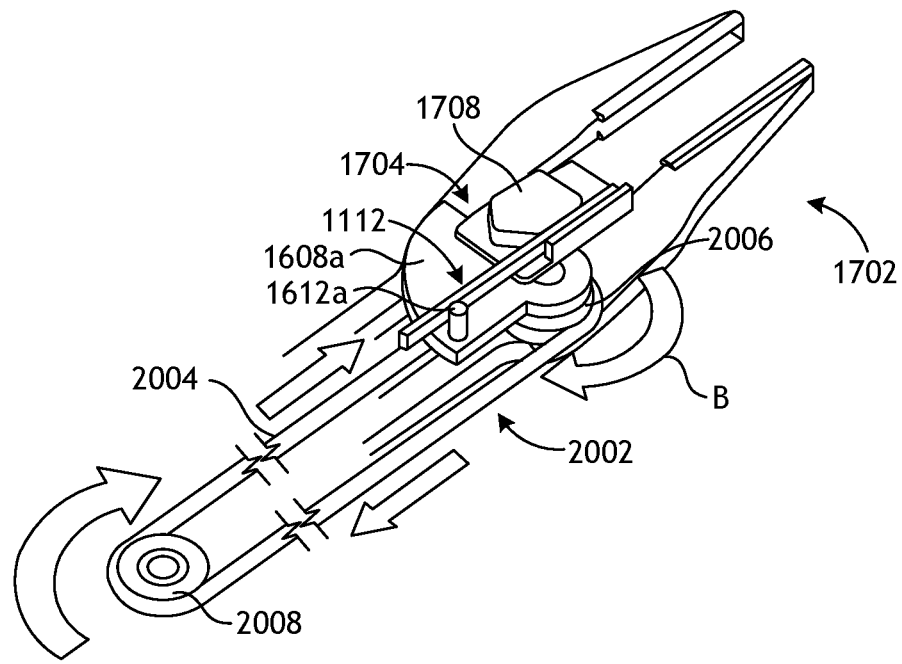
FIG. 20 depicts another example actuation mechanism that may be incorporated into an end effector and used to actuate a clip forming system.

FIG. 20 depicts another example actuation mechanism 2002 that may be used to actuate a clip forming system to transition unformed surgical clips to tissue-ready surgical clips. FIG. 20 shows the actuation mechanism 2002 incorporated into the end effector 1702 of FIGS. 17A-17E and used to actuate the system 1704. It will be appreciated, however, that the actuation mechanism 2002 may alternatively be incorporated into any of the end effectors described herein, without departing from the scope of the disclosure.

As illustrated, the actuation mechanism 2002 may include one or more drive cables 2004 extending to a distal pulley 2006 arranged at the system 1704. The drive cable(s) 2004 may be similar to the drive cables 808 of FIG. 8, for example. In the illustrated embodiment, a single drive cable 2004 loops around the distal pulley 2006 to provide rotational input configured to actuate the system 1704. In other embodiments, however, the drive cable 2004 may comprise two drive cables that extend to and antagonistically rotate the distal pulley 2006 to actuate the system 1704.

In the illustrated embodiment, the drive cable 2004 further loops around a proximal pulley 2008 configured to be rotated and convert its rotational movement to linear movement of the drive cable 2004. In some embodiments, the proximal pulley 2008 may be positioned in a drive housing (e.g., the drive housings 206, 606 of FIGS. 2 and 6, respectively) and may comprise, for example, a capstan pulley, such as any of the rotatable capstans 1002a-f of FIG. 10. In embodiments where the drive cable 2004 comprises two drive cables, the proximal pulley 2008 may comprise two capstan pulleys configured to cooperatively operate to actuate the system 1704. In embodiments with an articulable wrist, the drive cable 2004 may be configured to extend through the wrist to actuate the system 1704. In other embodiments, however, the distal pulley 2008 may be arranged distal to the wrist and driven (rotated) by another actuation mechanism operatively coupled to the distal pulley 2008 and extendable through the wrist.

Linear movement of the drive cable 2004 correspondingly rotates the distal pulley 2006, which may be operatively coupled (either directly or indirectly) to the outer ring 1608a such that rotation of the distal pulley 2006 correspondingly rotates the outer ring 1608a and the bending feature 1612a in the angular direction B. Consequently, actuating the drive cable 2004 correspondingly rotates the outer ring 1608a in the angular direction B and thereby causes the bending feature 1612a to progressively bend the surgical clip 1112 around the apex stop feature 1708 to the tissue-ready state.

Figure 21:
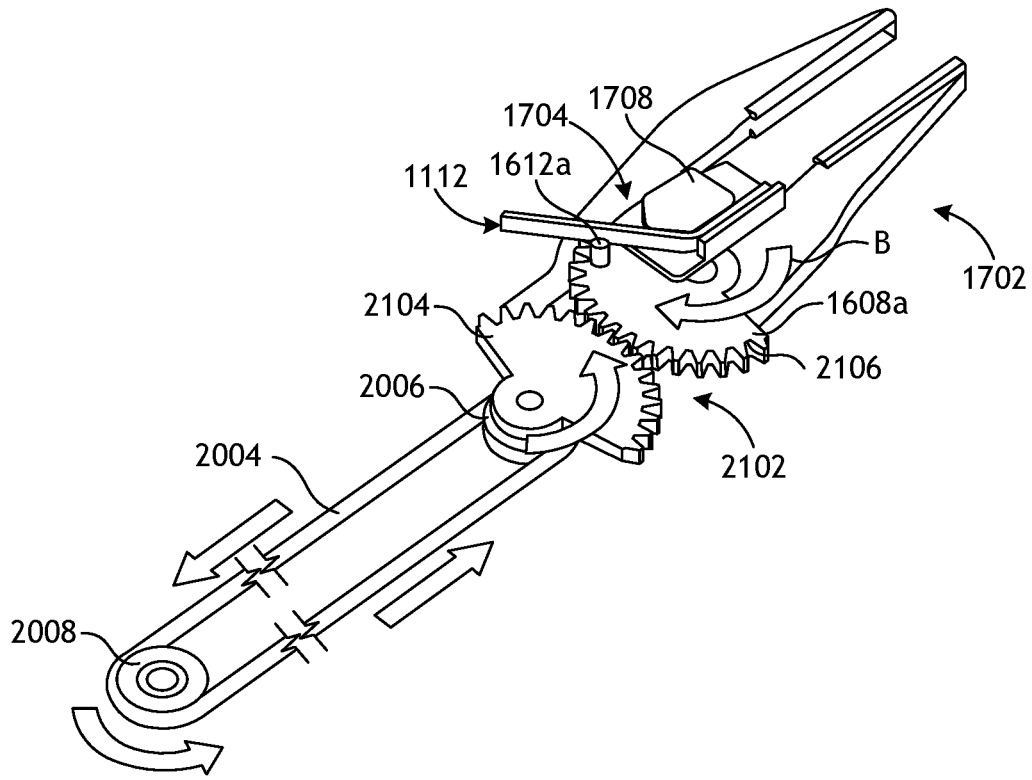
FIG. 21 depicts another example actuation mechanism that may be incorporated into an end effector and used to actuate a clip forming system.

FIG. 21 depicts another example actuation mechanism 2102 that may be used to actuate a clip forming system to transition unformed surgical clips to tissue-ready surgical clips. FIG. 21 shows the actuation mechanism 2102 incorporated into the end effector 1702 of FIGS. 17A-17E and used to actuate the system 1704. It will be appreciated, however, that the actuation mechanism 2102 may alternatively be incorporated into any of the end effectors described herein, without departing from the scope of the disclosure.

The actuation mechanism 2102 may be similar in some respects to the actuation mechanism 2002 of FIG. 20 and therefore may be best understood with reference thereto, where like numerals correspond to like components not described again. For example, the actuation mechanism 2102 may include the drive cable(s) 2004 extending to the distal pulley 2006, and the proximal pulley 2008 may be driven to convert its rotational motion to linear motion of the drive cable(s) 2004.

Linear movement of the drive cable 2004 correspondingly rotates the distal pulley 2006, which may be operatively coupled (either directly or indirectly) to a sector drive gear 2104 intermeshed with a sector driven gear 2106. The sector driven gear 2106 may be operatively coupled to (either directly or indirectly) or otherwise form part of the outer ring 1608a such that movement of the sector driven gear 2106 correspondingly rotates the outer ring 1608a and the bending feature 1612a in the angular direction B. Consequently, actuating the drive cable 2004 correspondingly rotates the outer ring 1608a in the angular direction B and thereby causes the bending feature 1612a to progressively bend the surgical clip 1112 around the apex stop feature 1708 to the tissue-ready state. As will be appreciated, the sector drive and driven gears 2104, 2106 may be replaced with a variety of other types of gears, such as corresponding spur gear, helical gears, or any suitable gear which transfers motion between two relatively planar drivetrains.

Figure 22A:
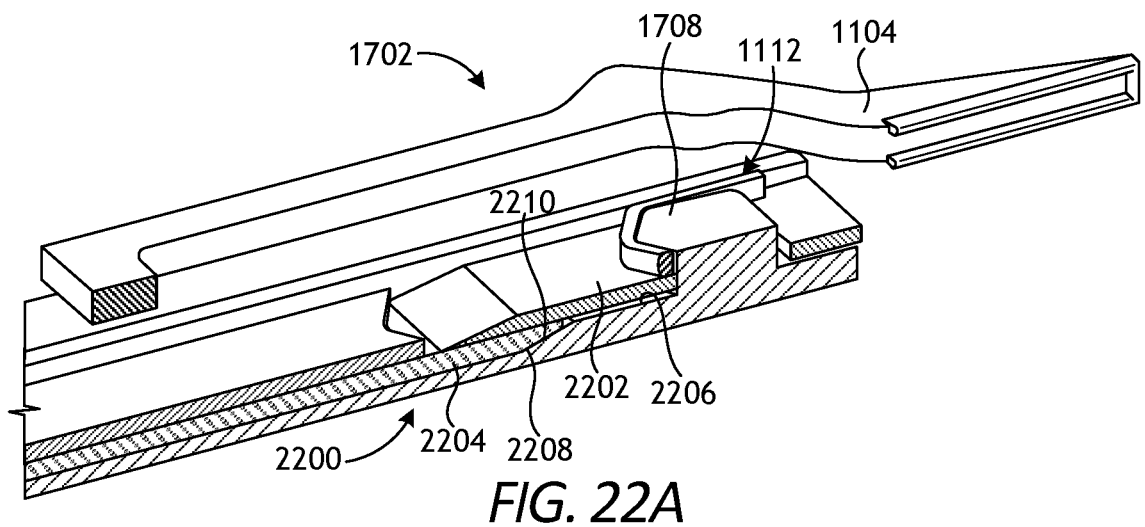
FIGS. 22A and 22B are partial cross-sectional side views of an example end effector feeding a surgical clip into jaws of a clip applier.
Figure 22B:
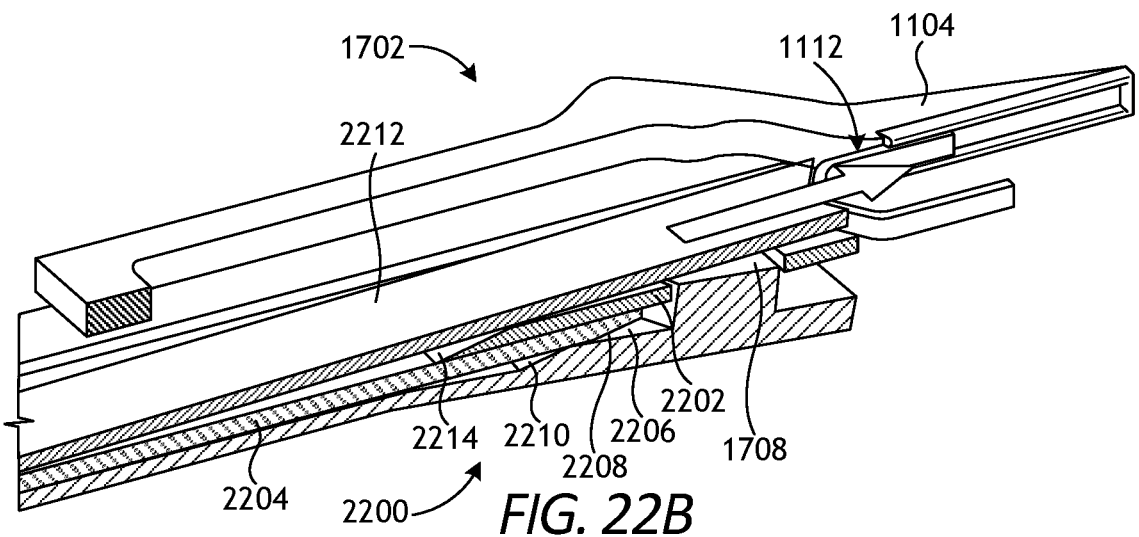

FIGS. 22A and 22B are partial cross-sectional side views of an example end effector and a clip bypass assembly 2200, according to one or more embodiments. More specifically, FIGS. 22A-22B depict the clip bypass assembly 2200 being incorporated into the end effector 1702 of FIGS. 17A-17E, but it will be appreciated that the clip bypass assembly 2200 may equally or alternatively be incorporated into any of the end effectors described herein, without departing from the scope of the disclosure. The clip bypass assembly 2200 may be configured to help tissue-ready surgical clips 1112 bypass a clip forming system, such as the clip forming system 1704 of FIGS. 17A-17E, to be introduced between the opposed jaw members 1104, 1106 (only the first jaw member 1104 is shown). The clip bypass assembly 2200 may be configured to help tissue-ready surgical clips 1112 bypass any of the clip forming systems described herein.

Referring first to FIG. 22A, as illustrated, the surgical clip 1112 has been bent around the apex stop feature 1708, as generally described above with reference to FIGS. 17A-17E. Once formed around the apex stop feature 1708, the surgical clip 1112 is unable to advance distally to the jaw members 1104, 1106 as the apex stop feature 1708 obstructs any distal advancement. To enable the surgical clip 1112 to advance distally past the apex stop feature 1708, the clip bypass assembly 2200 may be actuated. The clip bypass assembly 2200 may include a forming substrate 2202 and a wedge bar 2204. The forming substrate 2202 may be positioned atop or otherwise rest on a base surface 2206. In embodiments with the clip forming system 1704 of FIGS. 17A-17E, the base surface 2206 may comprise the upper surface of the clip forming jig 1609 of FIG. 17A. In other embodiments, however, the base surface 2206 may comprise the upper surface of the inner ring 1608a of FIG. 17A. In yet other embodiments, the base surface 2206 may comprise any other upper surface of the clip forming system 1704.

The forming substrate 2202 may be configured to provide a surface upon which the surgical clip 1112 may rest during and/or after being bent (formed) into the tissue-ready state.

In at least one embodiment, the forming substrate 2202 may at least partially circumscribe the apex stop feature 1708 and, therefore, may be moveable relative to the apex stop feature 1708.

The wedge bar 2204 may be configured to translate longitudinally and advance beneath the forming substrate 2202 and thereby elevate the forming substrate 2202 relative to the apex stop feature 1708. The wedge bar 2204 may extend to the end effector 1702 from a drive housing (e.g., one of the drive housings 206, 606 of FIGS. 2 and 6, respectively) where the wedge bar 2204 may be operatively coupled to an actuating mechanism or device configured to cause longitudinal translation of the wedge bar 2204. In one embodiment, for example, the wedge bar 2204 may be operatively coupled to and otherwise extend from one or more translatable driven gears, such as the second and third driven gears 504b,c of FIG. 5. In embodiments with an articulable wrist, the wedge bar 2204 may be made of a flexible material and extend through the wrist. Alternatively, the wedge bar 2204 may be operatively coupled to a cable-driven gearing arrangement positioned distal to the wrist and the associated drive cable(s) that moves the gear(s) extend(s) through the wrist.

In FIG. 22B, the wedge bar 2204 is shown advanced distally beneath the forming substrate 2202. The wedge bar 2204 may provide and otherwise define a ramped surface 2208 configured to slidably engage a corresponding ramped surface 2210 of the base surface 2206. As the wedge bar 2204 advances distally, the ramped surface 2208 slidingly engages the opposing ramped surface 2210 and thereby lifts the forming substrate 2202 off the base surface 2206 and correspondingly elevates the surgical clip 1112 above the apex stop feature 1708.

Once the surgical clip 1112 is elevated above the apex stop feature 1708, a feedbar 2212 may be actuated to distally advance the surgical clip 1112 to the jaw members 1104, 1106 (only the first jaw member 1104 is shown). In some embodiments, the forming substrate 2202 may also provide or otherwise define a ramped surface 2214 that the feedbar 2212 may slidably engage and ride up as it advances to engage and move the surgical clip 1112. The feedbar 2212 may be similar to the feedbar 1136 of FIG. 11D and, therefore, may extend to the end effector 1702 from a drive housing (e.g., the drive housings 206, 606 of FIGS. 2 and 6, respectively) where the feedbar 2212 may be operatively coupled to an actuating mechanism or device configured to cause longitudinal translation of the feedbar 2212. Alternatively, the feedbar 2212 may be operatively coupled to a cable-driven gearing arrangement positioned distal to an articulable wrist and the associated drive cable(s) that moves the gear(s) extend(s) through the wrist.

Figure 23A:
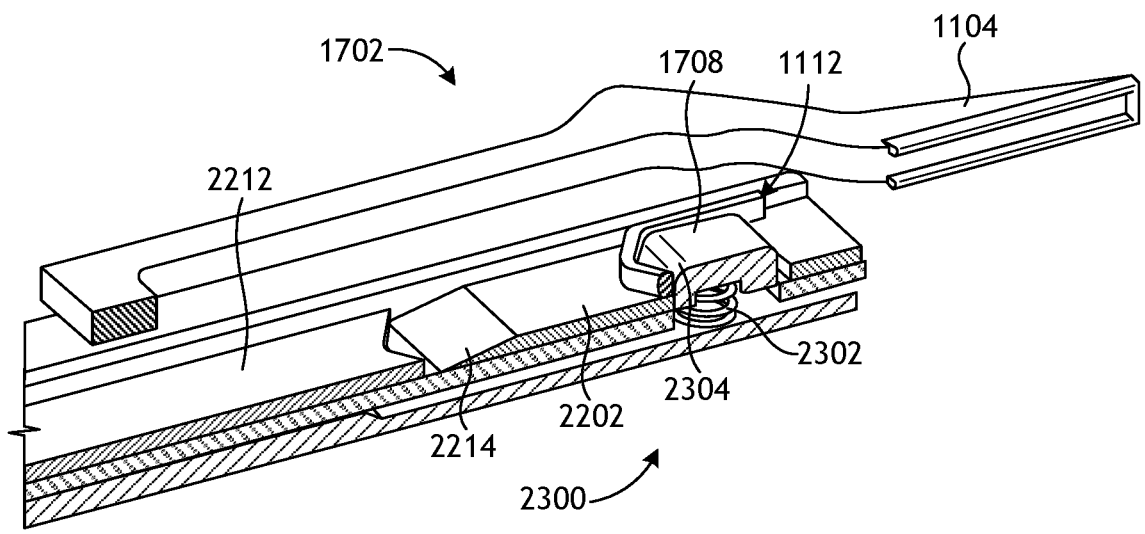
FIGS. 23A and 23B are partial cross-sectional side views of another example end effector feeding a surgical clip into jaws of a clip applier.
Figure 23B:
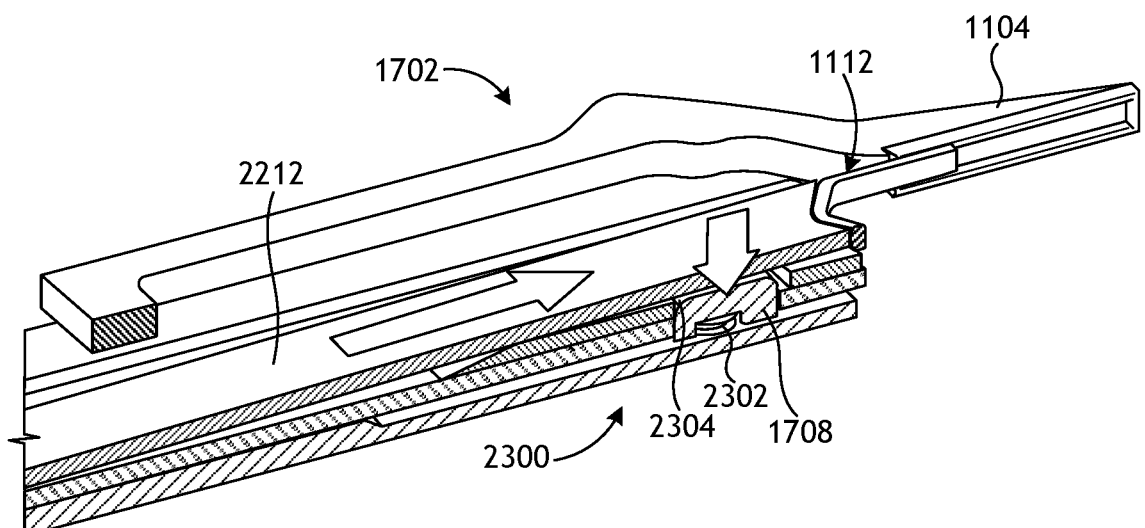

FIGS. 23A and 23B are partial cross-sectional side views of another example end effector and a clip bypass assembly 2300 for feeding a surgical clip into jaws of a clip applier, according to one or more embodiments. More specifically, FIGS. 23A-23B depict the clip bypass assembly 2300 incorporated into the end effector 1702 of FIGS. 17A-17E, but it will be appreciated that the clip bypass assembly 2300 may equally or alternatively be incorporated into any of the end effectors described herein, without departing from the scope of the disclosure. Similar to the clip bypass assembly 2200 of FIGS. 22A-22B, the clip bypass assembly 2300 may be configured to help tissue-ready surgical clips 1112 bypass a clip forming system, such as the clip forming system 1704 of FIGS. 17A-17E. The clip bypass assembly 2300 may be configured to help tissue-ready surgical clips 1112 bypass any of the clip forming systems described herein.

Referring first to FIG. 23A, as illustrated, the surgical clip 1112 has been bent around the apex stop feature 1708 to the tissue-ready state. The apex stop feature 1708, however, obstructs distal advancement of the surgical clip 1112. In the illustrated embodiment, the apex stop feature 1708 is compliantly biased with a biasing member 2302, such as a compression spring or the like. To enable the surgical clip 1112 to advance distally past the apex stop feature 1708, the clip bypass assembly 2300 may include the forming substrate 2202, which provides the ramped surface 2214 that enables the feedbar 2212 to slidably engage and ride up on top of the forming substrate 2212 when actuated. The apex stop feature 1708 may also provide and otherwise define an angled, rounded, or chamfered proximal surface 2304. When the feedbar 2212 applies an axial load on the surgical clip 1112, the surgical clip 1112 is urged against the rounded proximal surface 2304, which forces the apex stop feature 1708 downward and out of the way to elevate the surgical clip 1112 above the apex stop feature 1708.

In FIG. 23B, the feedbar 2212 is shown advanced distally and correspondingly advancing the surgical clip 1112 past the apex stop feature 1708 to be received within the jaw members 1104, 1106 (only the first jaw member 1104 is shown). The biasing member 2302 may be tuned to resist the forces necessary to transform the surgical clip 1112 to the tissue-ready state, but allow the feedbar 2212 to force the apex stop feature 1708 downward as the surgical clip 1112 is urged against the rounded proximal surface 2304. Once the biasing member 2302 is compressed, the feedbar 2212 may then be able to push the surgical clip 1112 distally past the apex stop feature 1708 and into the jaw members 1104, 1106. Upon retraction of the feedbar 2212, the spring force of the biasing member 2302 resets the apex stop feature 1708 to its natural state in preparation for forming another tissue-ready surgical clip.

Figure 24A:
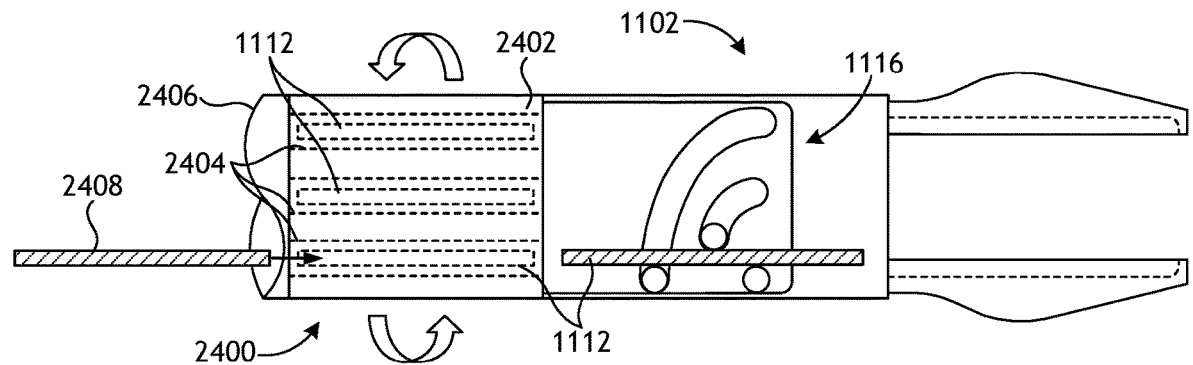
FIGS. 24A and 24B are top and isometric views, respectively, of an example clip feeding assembly for feeding unformed surgical clips into a clip forming system.
Figure 24B:
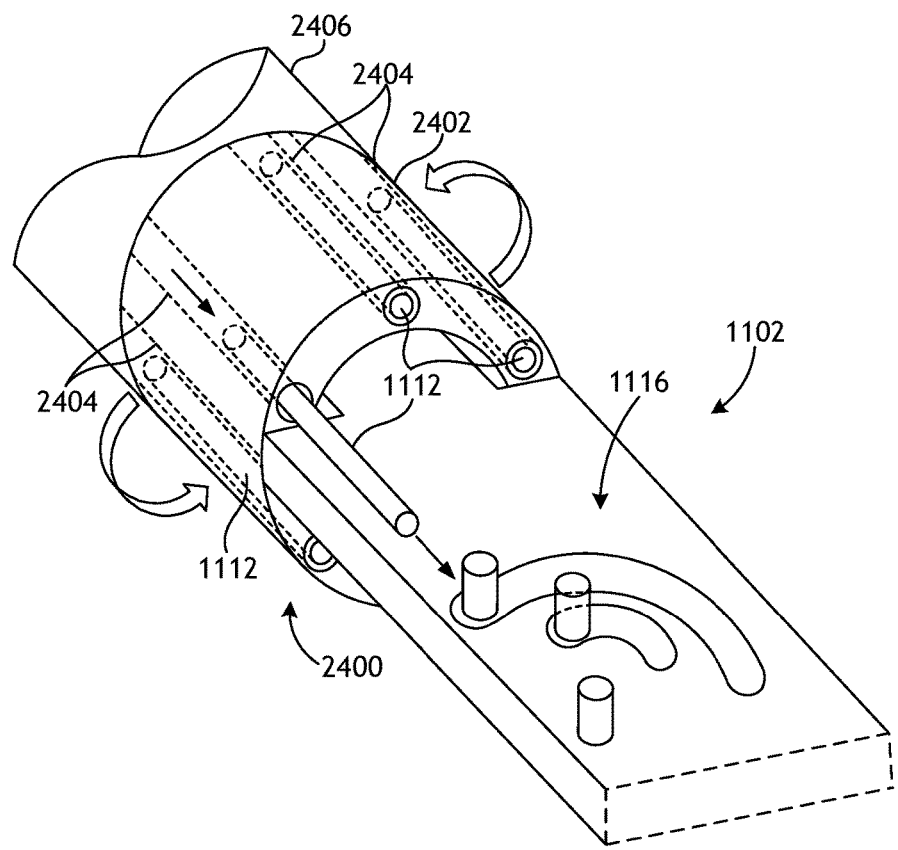

FIGS. 24A and 24B are top and isometric views, respectively, of an example clip feeding assembly 2400 for feeding unformed surgical clips into a clip forming system, according to one or more embodiments. More specifically, FIGS. 24A-24B depict the clip feeding assembly 2400 incorporated into the end effector 1102 of FIGS. 11A-11D, but it will be appreciated that the clip feeding assembly 2400 may alternatively be incorporated into any of the end effectors described herein, without departing from the scope of the disclosure. In some embodiments, the clip feeding assembly 2400 may be arranged distal to an articulable wrist (not shown).

As illustrated, the clip feeding assembly 2400 may include a revolving barrel 2402 that provides and otherwise defines a plurality of clip chambers 2404. The barrel 2402 may be generally cylindrical and the clip chambers 2404 may be equidistantly spaced around the barrel 2402. Each clip chamber 2404 may be sized to receive an unformed surgical clip 1112 therein. The number of clip chambers 2404 provided by the barrel 2402 may depend on the size of the barrel 2402 and is therefore not limited to the number depicted in the figures.

Actuating the clip feeding assembly 2400 may cause the barrel 2402 to rotate relative to the clip forming system 1116 and thereby selectively align the unformed surgical clips 1112 for discrete feeding into the clip forming system 1116. In some embodiments, for example, the barrel 2402 may be operatively coupled (either directly or indirectly) to a drive shaft 2406 that extends from a drive housing (e.g., one of the drive housings 206, 606 of FIGS. 2 and 6, respectively), and the drive shaft 2406 may be operatively coupled to an actuating mechanism or device positioned on the drive housing and configured to cause rotation of the drive shaft 2406, which correspondingly rotates the barrel 2402. In one embodiment, for example, the drive shaft 2406 may be operatively coupled to and otherwise extend from a helical gear arrangement, similar to the first drive and driven gears 502*a*, 504*a* of FIG. 5. In embodiments with an articulable wrist, the drive shaft 2406 may be made of a flexible material and capable of extending through the wrist.

In other embodiments, however, the barrel 2402 may be operatively coupled to a cable-driven gearing arrangement positioned distal to an articulable wrist and the associated drive cable(s) that moves the gear(s) extend(s) through the wrist. For example, the barrel 2402 may be operatively coupled to a worm gear assembly configured to be rotated to correspondingly rotate the barrel 2402. In yet other embodiments, the barrel 2402 may be rotated by being operatively coupled to a linkage that attaches to a drive input at a drive housing, and actuation of the drive input advances the linkage to the barrel 2402 and thereby indexes the barrel 2402 a predetermined angular distance, similar to operation of an actuatable ball-point pen. In such embodiments, the linkage may be flexible and capable of passing through an articulable joint, if needed. Moreover, in such embodiments, the linkage may terminate in a ratcheting mechanism comprising a series of opposing sloped surfaces engageable with a corresponding series of opposed sloped surfaces defined on the barrel 2402. Engagement between the opposed sloped surfaces causes the barrel 2402 to rotate. In even further embodiments, the barrel 2402 may be rotated using a pin-in-slot system, in which a drive bar with a pin is placed in an angled slot on the outside of the barrel 2402. Front-to-back actuation of the drive bar turns the barrel 2402 as the pin slides within the slot. Alternatively, the pin can be placed on the barrel 2402, and the slot on the drive bar.

A feedbar 2408 (FIG. 24A) may be configured to align with each chamber 2404 as the barrel 2402 rotates (indexes). The feedbar 2408 may be arranged to advance an aligned unformed surgical clip 1112 out of its corresponding chamber 2404 and distally toward the clip forming system 1116. More specifically, once a chamber 2404 is indexed to axially align with the feedbar 2408, the feedbar 2408 may be actuated and advanced distally into the chamber 2404. As the feedbar 2408 enters the chamber 2404, the unformed surgical clip 1112 is pushed out the opposing end and into the clip forming system 1116. In some embodiments, each time the feedbar 2408 is actuated (advanced distally and retracted), the barrel 2402 may simultaneously be indexed (rotated or ratcheted) by one chamber 2404 to thereby align the angularly adjacent chamber 2404 with the feedbar 2408.

The feedbar 2408 may be similar to the feedbar 1136 of FIG. 11D and, therefore, may extend to the end effector 1102 from a drive housing (e.g., the drive housings 206, 606 of FIGS. 2 and 6, respectively) where the feedbar 2408 may be operatively coupled to an actuating mechanism or device configured to cause longitudinal translation of the feedbar 2408. Alternatively, the feedbar 2408 may be operatively coupled to a cable-driven gearing arrangement positioned distal to an articulable wrist and the associated drive cable(s) that moves the gear(s) extend(s) through the wrist.

It should be noted that while the clip feeding assembly 2400 is shown being used in conjunction with the clip forming system 1116, the clip feeding assembly 2400 may be used in conjunction with any of the clip forming systems described herein, without departing from the scope of the disclosure.

FIGS. 25A and 25B are progressive top views of another example clip feeding assembly 2500 for feeding unformed surgical clips into a clip forming system, according to one or more embodiments. More specifically, FIGS. 25A-25B depict the clip feeding assembly 2500 incorporated into the end effector 1102 of FIGS. 11A-11D, but it will be appreciated that the clip feeding assembly 2500 may equally or alternatively be incorporated into any of the end effectors described herein, without departing from the scope of the disclosure. In some embodiments, the clip feeding assembly 2500 may be arranged distal to an articulable wrist (not shown).

In the illustrated embodiment, a continuous wire 2502 is conveyed to the end effector 1102 and the clip feeding assembly 2500 includes a cutting system 2504 configured to sever the wire 2502 and thereby form individual unformed surgical clips 1112. In some embodiments, the wire 2502 may be rigid enough and otherwise capable of extending through an articulable wrist. In such embodiments, the wire 2502 may originate, for example, from a spool or the like arranged proximal to the wrist, such as at a drive housing. In other embodiments, however, the wire 2502 may simply extend to the end effector 1102 and may be of sufficient length to provide a plurality of unformed surgical clips to the clip forming system 1116. The wire 2502 may be advanced distally to the end effector 1102 using any of the actuation devices or mechanisms described herein.

The cutting system 2504 may comprise any device or mechanism configured to sever the wire 2502. In the illustrated embodiment, for example, the cutting system 2504 includes a cutter 2506 and an anvil 2508. One or both of the cutter 2506 and the anvil 2508 may be actuatable and otherwise movable toward the other to sever the wire 2502. As shown in FIG. 25B, the cutter 2506 is configured to advance toward the anvil 2508 to sever the wire 2502. In other embodiments, however, the anvil 2508 may advance toward the cutter 2506 to sever the wire 2502, or both the cutter 2506 and the anvil 2508 may simultaneously move toward the other to sever the wire 2502.

In some embodiments, the wire 2502 may include a plurality of joints 2510 (FIG. 25A) at predetermined increments (locations) where the wire 2502 is to be severed to produce the unformed surgical clips 1112. In at least one embodiment, the joints 2510 may be locations where the wire 2502 has been scored or partially cut (weakened). In other embodiments, the joints 2510 connect a plurality of rods and may comprise a frangible material, such as a polymer or an elastomer coating. The frangible material may be rigid enough to enable the wire 2502 to be pushed to the end effector 1102, but weak enough to fail upon actuation of the cutting system 2504. In yet other embodiments, the wire 2502 may be soft or weak enough to tear at the joints 2510 once the clip forming system 1116 is actuated. In such embodiments, the components of the cutting system 2504 may simply operate as standards to hold the continuous wire 2502 in place during operation.

In some embodiments, actuation of the cutting system 2504 may form part of the stroke or actuation movement of the clip forming system 1116 for bending the clips. Consequently, an extra drive mechanism used to drive the cutting system 2504 may not be required since it will share the same drive mechanism as the clip forming system 1116. Moreover, it should be noted that while the clip feeding assembly 2500 and associated cutting system 2504 are shown being used in conjunction with the clip forming system 1116, the clip feeding assembly 2400 and the cutting system 2504 may be used in conjunction with any of the clip forming systems described herein, without departing from the scope of the disclosure.

FIGS. 26A-26C depict alternate embodiments for the cutting system 2504 of FIGS. 25A-25B, according to one or more embodiments. It is noted that the embodiments of the cutting system 2504 depicted in FIGS. 26A-26C are merely for illustrative purposes, and therefore should not be considered limiting of the present disclosure. Those skilled in the art will readily recognize that numerous variations of the cutting system 2504 may be employed, without departing from the scope of the disclosure.

In FIG. 26A, the cutting system 2504 includes the cutter 2506 and the anvil 2508. The cutter 2506 includes a blade 2602 located at an intermediate location on the cutter 2506. In other embodiments, however, the blade 2602 may be positioned at either end of the cutter 2506, without departing from the scope of the disclosure. In operation, the blade 2602 severs the continuous wire 2502 (FIGS. 25A-25B) as one or both of the cutter 2506 and the anvil 2508 advance toward each other.

In FIG. 26B, the cutting system 2504 includes two opposing cutters, shown as a first cutter 2506a and a second cutter 2506b. Each cutter 2506a,b includes a blade, shown as a first blade 2602a and 2602b, respectively. As illustrated, the blades 2602a,b are located at an intermediate location on the respective cutters 2506a,b, but could alternatively be positioned at other locations, without departing from the scope of the disclosure. In operation, the blades 2602a,b cooperatively sever the continuous wire 2502 (FIGS. 25A-25B) as one or both of the cutters 2506a,b advance toward each other.

In FIG. 26B, the cutting system 2504 includes two opposing cutters, shown as a first cutter 2506c and a second cutter 2506d. Each cutter 2506c,d includes a blade, shown as a first blade 2602c and a second blade 2602d, respectively. As illustrated, the blades 2602c,d each define a flat surface aligned with each other to help facilitate a cleaner cut of the continuous wire 2502 (FIGS. 25A-25B) as one or both of the cutters 2506c,d advance toward each other.

Embodiments disclosed herein include:

A. An end effector for a surgical clip applier that includes an elongate body, a clip forming system positioned within the body and arranged to receive an unformed surgical clip, an actuation mechanism operatively coupled to the clip forming system to actuate the clip forming system and thereby bend the unformed surgical clip into a tissue-ready surgical clip, and first and second jaw members positioned at a distal end of the body and arranged to receive the tissue-ready surgical clip for crimping.

B. A method of operating an end effector of a surgical clip applier that includes positioning the end effector adjacent a patient for operation, the end effector including an elongate body, a clip forming system positioned within the body, an actuation mechanism operatively coupled to the clip forming system, and first and second jaw members positioned at a distal end of the body. The method further includes advancing an unformed surgical clip to the clip forming system, actuating the clip forming system and thereby bending the unformed surgical clip into a tissue-ready surgical clip, advancing the tissue-ready surgical clip from the clip forming system to the first and second jaw members, and collapsing the first and second jaw members to crimp the tissue-ready surgical clip.

C. A surgical clip applier that includes a drive housing, an elongate shaft that extends from the drive housing, and an end effector arranged at a distal end of the elongate shaft, the end effector including an elongate body, a clip forming system positioned within the body and arranged to receive an unformed surgical clip, an actuation mechanism operatively coupled to the clip forming system to actuate the clip forming system and thereby bend the unformed surgical clip into a tissue-ready surgical clip, and first and second jaw members positioned at a distal end of the body and arranged to receive the tissue-ready surgical clip for crimping.

Each of embodiments A, B, and C may have one or more of the following additional elements in any combination: Element 1: further comprising a plurality of unformed surgical clips stored within the body distal to an articulable wrist, wherein the unformed surgical clip comprises one of the plurality of unformed surgical clips. Element 2: wherein the clip forming system comprises a forming plate, a clip receiver feature positioned on the forming plate and arranged to receive a distal end of the unformed surgical clip, an apex stop feature engageable with the unformed surgical clip to help form a crown of the tissue-ready surgical clip, and a bending feature movable relative to the clip receiver feature and engageable with the unformed surgical clip to bend the unformed surgical clip into the tissue-ready surgical clip. Element 3: further comprising at least one of one or more retention features provided on the unformed surgical clip and engageable with one or both of the clip receiver feature and the bending feature, and a detent provided on the unformed surgical clip and engageable with the apex stop feature. Element 4: wherein the forming plate defines a first arcuate slot and a second arcuate slot, and wherein the apex stop feature extends through and is translatable within the first arcuate slot, and the bending feature extends through and is translatable within the second arcuate slot. Element 5: wherein the forming plate comprises an outer ring that defines an arcuate slot and is rotatable relative to the clip receiver feature, an inner ring received within the arcuate slot and defining a post slot, and a substrate positioned on a bottom of the forming plate and defining a translation slot, wherein the bending feature extends from the outer ring such that rotational movement of the outer ring correspondingly moves the bending feature, and wherein the apex stop feature is slidably received within the translation slot and extends through the post slot such that movement of the inner ring correspondingly moves the apex stop feature within the translation slot. Element 6: wherein the forming plate comprises an upper plate that defines a cam slot and is rotatable relative to the clip receiver feature, and a substrate positioned on a bottom of the upper plate and defining a translation slot, wherein the bending feature extends from the upper plate such that rotational movement of the upper plate correspondingly moves the bending feature, and wherein the apex stop feature is slidably received within the translation slot and extends through the cam slot such that movement of the upper plate correspondingly moves the apex stop feature within the cam slot and the translation slot. Element 7: wherein the forming plate comprises an outer ring rotatable relative to the clip receiver feature, and an inner ring positioned within the outer ring, wherein the bending feature extends from the outer ring such that rotational movement of the outer ring correspondingly moves the bending feature, and wherein the clip receiver feature and the apex stop feature are operatively coupled to the inner ring and remain stationary as the outer ring rotates. Element 8: further comprising a clip forming jig positioned on the inner ring, wherein the clip receiver feature and the apex stop feature extend from the clip forming jig. Element 9: wherein the apex stop feature comprises a polygonal-shaped structure that provides a bend pattern for the tissue-ready surgical clip. Element 10: further comprising a clip bypass assembly actuatable to elevate the tissue-ready surgical clip above the apex stop feature to enable the tissue-ready surgical clip to distally traverse the clip forming system. Element 11: further comprising a clip feeding assembly positioned proximal to the clip forming system and actuatable to feed the unformed surgical clip into the clip forming system. Element 12: wherein the unformed surgical clip comprises one of a plurality of unformed surgical clips, and the clip feeding assembly further comprises a rotatable barrel that defines a plurality of clip chambers, each clip chamber being sized to receive a discrete unformed surgical clip of the plurality of surgical clips, and a feedbar alignable with each clip chamber as the barrel rotates and actuatable to distally advance the discrete unformed surgical clip from each clip chamber and toward the clip forming system. Element 13: wherein the unformed surgical clip is formed from a wire conveyable to the clip forming system and severable to generate a plurality of unformed surgical clips. Element 14: wherein the clip feeding assembly includes a cutting system actuatable to sever the wire and thereby generate the plurality of unformed surgical clips.

Element 15: wherein the clip forming system includes, a forming plate, a clip receiver feature positioned on the forming plate, an apex stop feature, and a bending feature, and wherein actuating the clip forming system comprises receiving a distal end of the unformed surgical clip with the clip receiver feature, moving the bending feature relative to the clip receiver feature and thereby engaging the bending feature against the unformed surgical clip, and bending the unformed surgical clip about the apex stop feature to help form a crown of the tissue-ready surgical clip. Element 16: further comprising actuating a clip feeding assembly positioned proximal to the clip forming system and thereby feeding the unformed surgical clip into the clip forming system.

Element 17: further comprising an articulable wrist joint interposing the end effector and the elongate shaft.

By way of non-limiting example, exemplary combinations applicable to A, B, and C include: Element 2 with Element 3; Element 2 with Element 4; Element 2 with Element 5; Element 2 with Element 6; Element 2 with Element 7; Element 7 with Element 8; Element 7 with Element 9; Element 11 with Element 12; Element 11 with Element 13; Element 13 with Element 14; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical clip applier, comprising:
   an elongate body;
   an unformed surgical clip at least partially housed within the body and comprising a substantially straight length of an elongate material;
   a clip forming system positioned within the body and arranged to receive the unformed surgical clip;
   an actuation mechanism operatively coupled to the clip forming system to actuate the clip forming system and thereby bend the unformed surgical clip into a tissue-ready surgical clip; and
   first and second jaw members positioned at a distal end of the body and arranged to receive the tissue-ready surgical clip for crimping.

2. The end effector of claim 1, further comprising a plurality of unformed surgical clips stored within the body distal to an articulable wrist, wherein the unformed surgical clip comprises one of the plurality of unformed surgical clips.

3. The end effector of claim 1, wherein the clip forming system comprises:
   a forming plate;
   a clip receiver feature positioned on the forming plate and arranged to receive a distal end of the unformed surgical clip;
   an apex stop feature engageable with the unformed surgical clip to help form a crown of the tissue-ready surgical clip; and
   a bending feature movable relative to the clip receiver feature and engageable with the unformed surgical clip to bend the unformed surgical clip into the tissue-ready surgical clip.

4. The end effector of claim 3, further comprising at least one of:
   one or more retention features provided on the unformed surgical clip and engageable with one or both of the clip receiver feature and the bending feature; and
   a detent provided on the unformed surgical clip and engageable with the apex stop feature.

5. The end effector of claim 3, wherein the forming plate defines a first arcuate slot and a second arcuate slot, and wherein the apex stop feature extends through and is translatable within the first arcuate slot, and the bending feature extends through and is translatable within the second arcuate slot.

6. The end effector of claim 3, wherein the forming plate comprises:
an outer ring that defines an arcuate slot and is rotatable relative to the clip receiver feature;
an inner ring received within the arcuate slot and defining a post slot; and
a substrate positioned on a bottom of the forming plate and defining a translation slot,
wherein the bending feature extends from the outer ring such that rotational movement of the outer ring correspondingly moves the bending feature, and
wherein the apex stop feature is slidably received within the translation slot and extends through the post slot such that movement of the inner ring correspondingly moves the apex stop feature within the translation slot.

7. The end effector of claim 3, wherein the forming plate comprises:
an upper plate that defines a cam slot and is rotatable relative to the clip receiver feature; and
a substrate positioned on a bottom of the upper plate and defining a translation slot,
wherein the bending feature extends from the upper plate such that rotational movement of the upper plate correspondingly moves the bending feature, and
wherein the apex stop feature is slidably received within the translation slot and extends through the cam slot such that movement of the upper plate correspondingly moves the apex stop feature within the cam slot and the translation slot.

8. The end effector of claim 3, wherein the forming plate comprises:
an outer ring rotatable relative to the clip receiver feature; and
an inner ring positioned within the outer ring,
wherein the bending feature extends from the outer ring such that rotational movement of the outer ring correspondingly moves the bending feature, and
wherein the clip receiver feature and the apex stop feature are operatively coupled to the inner ring and remain stationary as the outer ring rotates.

9. The end effector of claim 8, further comprising a clip forming jig positioned on the inner ring, wherein the clip receiver feature and the apex stop feature extend from the clip forming jig.

10. The end effector of claim 8, wherein the apex stop feature comprises a polygonal-shaped structure that provides a bend pattern for the tissue-ready surgical clip.

11. The end effector of claim 1, further comprising a clip bypass assembly actuatable to elevate the tissue-ready surgical clip above the apex stop feature to enable the tissue-ready surgical clip to distally traverse the clip forming system.

12. The end effector of claim 1, further comprising a clip feeding assembly positioned proximal to the clip forming system and actuatable to feed the unformed surgical clip into the clip forming system.

13. The end effector of claim 12, wherein the unformed surgical clip comprises one of a plurality of unformed surgical clips, and the clip feeding assembly further comprises:
a rotatable barrel that defines a plurality of clip chambers, each clip chamber being sized to receive a discrete unformed surgical clip of the plurality of surgical clips; and
a feedbar alignable with each clip chamber as the barrel rotates and actuatable to distally advance the discrete unformed surgical clip from each clip chamber and toward the clip forming system.

14. The end effector of claim 12, wherein the unformed surgical clip is formed from a wire conveyable to the clip forming system and severable to generate a plurality of unformed surgical clips.

15. The end effector of claim 14, wherein the clip feeding assembly includes a cutting system actuatable to sever the wire and thereby generate the plurality of unformed surgical clips.

16. A method of operating an end effector of a surgical clip applier, comprising:
positioning the end effector adjacent a patient for operation, the end effector including:
an elongate body;
a clip forming system positioned within the body;
an actuation mechanism operatively coupled to the clip forming system; and
first and second jaw members positioned at a distal end of the body;
advancing an unformed surgical clip to the clip forming system;
actuating the clip forming system and thereby bending the unformed surgical clip into a tissue-ready surgical clip;
advancing the tissue-ready surgical clip from the clip forming system to the first and second jaw members; and
collapsing the first and second jaw members to crimp the tissue-ready surgical clip.

17. The method of claim 16, wherein the clip forming system includes, a forming plate, a clip receiver feature positioned on the forming plate, an apex stop feature, and a bending feature, and wherein actuating the clip forming system comprises:
receiving a distal end of the unformed surgical clip with the clip receiver feature;
moving the bending feature relative to the clip receiver feature and thereby engaging the bending feature against the unformed surgical clip; and
bending the unformed surgical clip about the apex stop feature to help form a crown of the tissue-ready surgical clip.

18. The method of claim 17, further comprising actuating a clip feeding assembly positioned proximal to the clip forming system and thereby feeding the unformed surgical clip into the clip forming system.

19. A surgical clip applier, comprising:
a drive housing;
an elongate shaft that extends from the drive housing; and
an end effector arranged at a distal end of the elongate shaft, the end effector including:
an elongate body;
an unformed surgical clip at least partially housed within the body and comprising a substantially straight length of an elongate material;
a clip forming system positioned within the body and arranged to receive the unformed surgical clip;
an actuation mechanism operatively coupled to the clip forming system to actuate the clip forming system and thereby bend the unformed surgical clip into a tissue-ready surgical clip; and first and second jaw members positioned at a distal end of the body and arranged to receive the tissue-ready surgical clip for crimping.

20. The surgical clip applier of claim 19, further comprising an articulable wrist joint interposing the end effector and the elongate shaft.

* * * * *